(12) United States Patent
Poupart et al.

(10) Patent No.: US 7,838,537 B2
(45) Date of Patent: Nov. 23, 2010

(54) VIRAL POLYMERASE INHIBITORS

(75) Inventors: Marc-André Poupart, Laval (CA);
Pierre Louis Beaulieu, Rosemére (CA);
Jean Rancourt, Laval (CA)

(73) Assignee: Boehringer Ingelheim International GmbH (DE)

( * ) Notice: Subject to any disclaimer, the term of this patent is extended or adjusted under 35 U.S.C. 154(b) by 0 days.

(21) Appl. No.: 11/948,239

(22) Filed: Nov. 30, 2007

(65) Prior Publication Data
US 2008/0119490 A1 May 22, 2008

Related U.S. Application Data

(60) Division of application No. 11/405,144, filed on Apr. 17, 2006, now Pat. No. 7,323,470, which is a continuation of application No. 10/755,544, filed on Jan. 12, 2004, now Pat. No. 7,098,231.

(60) Provisional application No. 60/441,674, filed on Jan. 22, 2003.

(51) Int. Cl.
*A61K 31/4436* (2006.01)
*A61K 31/381* (2006.01)
*C07D 409/04* (2006.01)
*C07D 333/52* (2006.01)

(52) U.S. Cl. .................. 514/337; 514/443; 546/281.1; 549/57

(58) Field of Classification Search ............ 514/255.05, 514/339, 414, 397, 443; 546/277.4, 278.1; 544/405; 548/466, 453; 549/58
See application file for complete search history.

(56) References Cited

U.S. PATENT DOCUMENTS

| | | |
|---|---|---|
| 3,565,912 A | 2/1971 | Szmuszkovicz |
| 4,003,908 A | 1/1977 | Denzel et al. |
| 4,146,725 A | 3/1979 | Meyer et al. |
| 4,250,317 A | 2/1981 | Meyer et al. |
| 4,252,803 A | 2/1981 | Webb |
| 4,264,325 A | 4/1981 | Meyer et al. |
| 4,360,679 A | 11/1982 | Meyer et al. |
| 4,384,121 A | 5/1983 | Meyer |
| 4,432,886 A | 2/1984 | Meyer |
| 4,433,975 A | 2/1984 | Meyer |
| 4,590,200 A | 5/1986 | Cross et al. |
| 4,740,519 A | 4/1988 | Shroot et al. |
| 4,859,684 A | 8/1989 | Raeymaekers et al. |
| 4,898,863 A | 2/1990 | Brown et al. |
| 4,920,140 A | 4/1990 | Shroot et al. |
| 5,059,621 A | 10/1991 | Shroot et al. |
| 5,216,003 A | 6/1993 | Vazquez |
| 5,410,061 A | 4/1995 | Gilmore et al. |
| 5,482,956 A | 1/1996 | Lunkenheimer et al. |
| 5,527,819 A | 6/1996 | Williams et al. |
| 5,661,159 A * | 8/1997 | Matsuo et al. ............... 514/314 |
| 5,817,689 A | 10/1998 | Kato et al. |
| 5,866,594 A | 2/1999 | Endo et al. |
| 5,912,260 A | 6/1999 | Kalindjian et al. |
| 5,932,743 A | 8/1999 | Collini et al. |
| 6,063,806 A | 5/2000 | Kamiya et al. |
| 6,069,156 A | 5/2000 | Oku et al. |
| 6,169,107 B1 | 1/2001 | Kitano et al. |
| 6,184,238 B1 | 2/2001 | Takano et al. |
| 6,211,177 B1 | 4/2001 | Sperl et al. |
| 6,228,868 B1 | 5/2001 | Gwaltney, II et al. |
| 6,358,992 B1 | 3/2002 | Pamukcu et al. |
| 6,399,644 B1 | 6/2002 | Wexler et al. |
| 6,407,102 B1 | 6/2002 | Mahboobi et al. |
| 6,448,281 B1 | 9/2002 | Beaulieu et al. |
| 6,455,525 B1 | 9/2002 | Singh et al. |
| 6,479,508 B1 | 11/2002 | Beaulieu et al. |
| 6,579,882 B2 | 6/2003 | Stewart et al. |
| 6,608,070 B1 | 8/2003 | Nakao et al. |
| 6,770,643 B2 | 8/2004 | Cox et al. |
| 6,770,666 B2 | 8/2004 | Hashimoto et al. |
| 6,794,404 B2 | 9/2004 | Beaulieu et al. |
| 6,897,207 B2 | 5/2005 | Cox et al. |
| 7,098,231 B2 | 8/2006 | Poupart et al. |
| 7,112,600 B1 | 9/2006 | Hashimoto et al. |
| 7,223,785 B2 | 5/2007 | Beaulieu et al. |
| 7,241,801 B2 | 7/2007 | Beaulieu et al. |
| 7,323,470 B2 * | 1/2008 | Poupart et al. ......... 514/255.05 |
| 7,332,614 B2 | 2/2008 | Khodabocus et al. |

(Continued)

FOREIGN PATENT DOCUMENTS

CA    1111695    11/1981

(Continued)

OTHER PUBLICATIONS

Lauer, G., et al., "Hepatitis C Virus Infection", N. Engl. J. Med., vol. 345 (1), pp. 41-52 (Jul. 2001).

(Continued)

*Primary Examiner*—Kamal A Saeed
*Assistant Examiner*—Kristin Bianchi
(74) *Attorney, Agent, or Firm*—Michael P. Morris; David A. Dow

(57) ABSTRACT

An isomer, enantiomer, diastereoisomer or tautomer of a compound, represented by formula I:

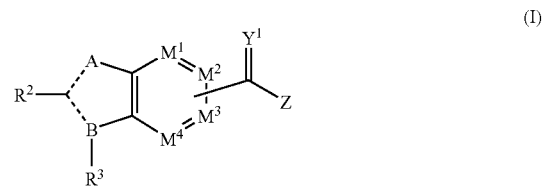

wherein A, B, $R^2$, $R^3$, $M^1$, $M^2$, $M^3$, $M^4$, $Y^1$ and Z are as defined in claim 1, or a salt thereof, as an inhibitor of HCV NS5B polymerase.

39 Claims, No Drawings

U.S. PATENT DOCUMENTS

| | | |
|---|---|---|
| 2001/0039286 A1 | 11/2001 | Dinnell et al. |
| 2002/0173527 A1 | 11/2002 | Astles |
| 2003/0050320 A1 | 3/2003 | Hashimoto et al. |
| 2003/0108862 A1 | 6/2003 | Kukolj et al. |
| 2003/0134853 A1* | 7/2003 | Priestley et al. .......... 514/233.5 |
| 2003/0176433 A1 | 9/2003 | Beaulieu et al. |
| 2003/0232816 A1 | 12/2003 | Beaulieu et al. |
| 2003/0236251 A1 | 12/2003 | Beaulieu et al. |
| 2004/0024190 A1 | 2/2004 | Beaulieu et al. |
| 2004/0082635 A1 | 4/2004 | Hashimoto et al. |
| 2004/0097438 A1 | 5/2004 | Hashimoto et al. |
| 2004/0110126 A1 | 6/2004 | Kukolj et al. |
| 2004/0171833 A1 | 9/2004 | Buchwald et al. |
| 2004/0224955 A1 | 11/2004 | Beaulieu et al. |
| 2005/0032875 A1 | 2/2005 | Wolleb et al. |
| 2005/0209465 A1 | 9/2005 | Li et al. |
| 2005/0222236 A1 | 10/2005 | Tsantrizos et al. |
| 2006/0160798 A1 | 7/2006 | Beaulieu et al. |
| 2006/0183752 A1 | 8/2006 | Khodabocus et al. |
| 2006/0293306 A1 | 12/2006 | Beaulieu et al. |
| 2007/0142380 A1 | 6/2007 | Beaulieu et al. |
| 2007/0249629 A1 | 10/2007 | Beaulieu et al. |
| 2008/0119490 A1 | 5/2008 | Poupart et al. |
| 2009/0087409 A1 | 4/2009 | Beaulieu et al. |
| 2009/0170859 A1 | 7/2009 | Tsantrizos et al. |

FOREIGN PATENT DOCUMENTS

| | | |
|---|---|---|
| CA | 2150812 | 6/1994 |
| CA | 2158996 | 10/1994 |
| CA | 2143040 | 8/1995 |
| CA | 2124169 | 11/1995 |
| CA | 2164394 | 6/1996 |
| CA | 2223585 | 12/1996 |
| CA | 2241186 | 6/1997 |
| CA | 2352871 A1 | 6/2000 |
| CA | 2389165 | 5/2001 |
| CA | 2363274 | 7/2001 |
| CA | 2412718 | 1/2002 |
| CA | 2448737 | 1/2003 |
| CA | 2449180 | 2/2003 |
| CH | 511873 | 8/1971 |
| DE | 2641060 | 3/1978 |
| DE | 3522230 | 1/1987 |
| DE | 19507913 | 9/1996 |
| EP | 10063 | 4/1980 |
| EP | 0011824 | 6/1980 |
| EP | 12291 | 6/1980 |
| EP | 14411 | 8/1980 |
| EP | 50957 | 5/1982 |
| EP | 73663 | 3/1983 |
| EP | 209707 | 1/1987 |
| EP | 242167 | 10/1987 |
| EP | 318084 | 5/1989 |
| EP | 353606 | 2/1990 |
| EP | 429240 | 5/1991 |
| EP | 439356 | 7/1991 |
| EP | 459334 | 12/1991 |
| EP | 0 539 117 A1 | 4/1993 |
| EP | 546713 | 6/1993 |
| EP | 549175 | 6/1993 |
| EP | 563910 | 10/1993 |
| EP | 583665 | 2/1994 |
| EP | 607439 | 7/1994 |
| EP | 615159 | 9/1994 |
| EP | 750226 | 12/1996 |
| EP | 0801059 | 10/1997 |
| EP | 987250 | 3/2000 |
| EP | 1 142 880 A1 | 10/2001 |
| EP | 1 162 196 A1 | 12/2001 |
| EP | 1256628 A2 | 11/2002 |
| FR | 1604809 | 4/1972 |
| FR | 2291749 | 6/1976 |
| GB | 602426 A | 5/1948 |
| GB | 1094903 | 12/1967 |
| GB | 1186504 | 4/1970 |
| GB | 1436089 | 5/1976 |
| GB | 1509527 | 5/1978 |
| GB | 2118552 | 11/1983 |
| GB | 2164648 | 3/1986 |
| GB | 2197320 | 5/1988 |
| GB | 2203420 | 10/1988 |
| JP | 60149502 | 8/1985 |
| JP | 61085360 | 4/1986 |
| JP | 3156444 | 7/1991 |
| JP | 5239036 | 9/1993 |
| JP | 6161064 | 6/1994 |
| JP | 6186703 | 7/1994 |
| JP | 6186705 | 7/1994 |
| JP | 6186706 | 7/1994 |
| JP | 6194794 | 7/1994 |
| JP | 6239841 | 8/1994 |
| JP | 6297858 | 10/1994 |
| JP | 7140604 | 6/1995 |
| JP | 7228530 | 8/1995 |
| JP | 9124632 | 5/1997 |
| JP | 09124632 A | 5/1997 |
| JP | 9328678 | 12/1997 |
| JP | 10067682 | 3/1998 |
| JP | 10114654 | 5/1998 |
| JP | 10204059 | 8/1998 |
| JP | 10265478 | 10/1998 |
| JP | 11021693 | 1/1999 |
| JP | 115003445 | 3/1999 |
| JP | 11177218 | 7/1999 |
| JP | 2001122855 | 5/2001 |
| WO | 9116313 | 10/1991 |
| WO | 9210097 | 6/1992 |
| WO | 9306828 | 4/1993 |
| WO | 9411349 | 5/1994 |
| WO | 9507263 | 3/1995 |
| WO | 9616938 | 6/1996 |
| WO | 9632379 | 10/1996 |
| WO | 9639391 | 12/1996 |
| WO | 9712613 | 4/1997 |
| WO | 9744319 | 11/1997 |
| WO | 9748697 | 12/1997 |
| WO | 9801436 | 1/1998 |
| WO | 9808847 | 3/1998 |
| WO | 9829408 | 7/1998 |
| WO | 9837069 | 8/1998 |
| WO | 9837079 | 8/1998 |
| WO | 1998039287 A1 | 9/1998 |
| WO | 9928297 | 6/1999 |
| WO | 9929660 | 6/1999 |
| WO | 9929661 | 6/1999 |
| WO | 9929843 A1 | 6/1999 |
| WO | 9935130 A1 | 7/1999 |
| WO | 9951781 | 10/1999 |
| WO | 9957117 A2 | 11/1999 |
| WO | 9961020 | 12/1999 |
| WO | 9965886 | 12/1999 |
| WO | 0006529 | 2/2000 |
| WO | 0006556 | 2/2000 |
| WO | 00006566 | 2/2000 |
| WO | 0010573 | 3/2000 |
| WO | 0013708 | 3/2000 |
| WO | 0018231 | 4/2000 |
| WO | 0026202 | 5/2000 |
| WO | 0027846 | 5/2000 |
| WO | 2000034277 A1 | 6/2000 |
| WO | 0130774 | 5/2001 |
| WO | 0132653 | 5/2001 |
| WO | 0147883 | 7/2001 |

| | | |
|---|---|---|
| WO | 0147922 | 7/2001 |
| WO | 0151487 | 7/2001 |
| WO | 0185172 | 11/2001 |
| WO | 0187885 | 11/2001 |
| WO | 0190121 | 11/2001 |
| WO | 0206246 | 1/2002 |
| WO | WO 02/04425 A2 | 1/2002 |
| WO | 2002026228 A1 | 4/2002 |
| WO | 02057287 | 7/2002 |
| WO | 02057425 | 7/2002 |
| WO | 02059118 | 8/2002 |
| WO | 02069903 | 9/2002 |
| WO | 02070739 | 9/2002 |
| WO | 02098424 | 12/2002 |
| WO | 02100846 | 12/2002 |
| WO | 02100851 | 12/2002 |
| WO | 03000254 | 1/2003 |
| WO | WO 03/007945 A1 | 1/2003 |
| WO | WO 03/014377 A2 | 1/2003 |
| WO | 03/010141 | 2/2003 |
| WO | WO 03/010140 A2 | 2/2003 |
| WO | 03/018555 | 3/2003 |
| WO | 03026587 | 4/2003 |
| WO | 03040112 | 5/2003 |
| WO | 03101993 | 12/2003 |
| WO | 04005286 | 1/2004 |
| WO | 2004005286 | 1/2004 |
| WO | 2004/064925 | 8/2004 |
| WO | 2004/065367 | 8/2004 |
| WO | 04087714 | 10/2004 |
| WO | 2004087714 | 10/2004 |
| WO | 2005/012288 | 2/2005 |
| WO | 05014543 | 2/2005 |
| WO | 2005014543 | 2/2005 |
| WO | 2005/080388 | 9/2005 |

OTHER PUBLICATIONS

CA Abstract. Zimmermann, et al., Archiv der Pharmazie (Weinheim, Germany) (1976), 309(7), pp. 597-600; CA 86:43587, 1977.

Hijkata, M., et al., "Gene mapping of the putative structural region of the hepatitis C virus genome by in vitro processing analysis". Proc. Natl. Acad. Sci. USA, vol. 88, Jul. 1991, Biochemistry, pp. 5547-5551.

Hijkata, M., et al., "Two distinct proteinase activities required for the processing of a putative nonstructural precursor protein of hepatitis C virus". Journal of Virology, Aug. 1993, Vo. 67, No. 8, pp. 4665-4675.

Hishmat, O. H., et al; "Synthesis of Pharmacologically Active Indoles"; Bolletino Chimico Farmaceutico (1999), 183 (6), pp. 259-266 (XP-002233311).

Hoofnagle, J.H.; 1997; Hepatology 26: 15S-20S.

Hulme, C., et al; "The Synthesis and Biological Evaluation of a Novel Series of Indole PDE4 Inhibitors I"; Bioorganic & Medicinal Chemistry Letters 8 (1998), pp. 1867-1872 (XP-002233861).

Ishiyama, T., Murata, M., Miyaura, N.; "Palladium(0)-Catalyzed Cross-Coupling Reaction of Alkoxydiboron with Haloarenes: A Direct Procedure for Arylboronic Esters;" J. Org. Chem. 1995, 60, 7508.

Kim, D. W., et al., "C-terminal domain of the hepatitis C virus NS3 protein contains an RNA helicase activity". Biochemical & Biophysical Research Communications, vol. 215, No. 1, 1995, pp. 160-166.

Kim, J.E., et al., "Subcellular localization of hepatitis C viral proteins in mammalian cells". Arch Virol., 1999, 144, pp. 329.343.

Kolykhalov, A.A. et al,"Hepatitis C Virus-Encoded Enzymatic Activities and Conserved RNA Elements in the 3' nontranslated Region are Essential for Virus Replication in Vivo", J. Virology, 2000, 74(4): 2046-2051.

Kwong, A. D., et al., "Hepatitis C virus NS3/4A protease". Antiviral Research, 40, 1998, pp. 1-18.

Lemon, S.H.; Honda, M.; "Internal Ribosome Entry Sites within the RNA Genomes of Hepatitis C Virus and Other Flaviviruses;" 1997; Semin. Virol. 8: 274-288.

Lesburg, C.A., et al., "Crystal structure of the RNA-dependent RNA polymerase from hepatitis C virus reveals a fully encircled active site". Nature Sructural Biology, vol. 6, No. 10, 1999, pp. 937-943.

Levin, Jules, "Safety, Pharmacokinetics and Antiviral effects of Boehringer Ingelheim BILB 1941, a Novel HCV RNA Polymerase, After 5 days Oral treatment in Patients with Chronic Hepatitis C", www.natap.org/2007/EASL/EASL_48. htm EASL 42nd Mtg. of Euruopean Association for the Study of Liver Diseases, Barcelona, Spain Apr. 11-15, 2007.

Lindsay, K.L.; "Therapy of Hepatitis C: Overview;" 1997; Hepatology 26: 71S-77S.

Lohmann, V. et al, "Replication of Subgenomic Hepatitis C Virus RNAs in a Hepatoma Cell Line" Science, 1999, 285: 110-113.

Lohmann, V., et al., "Biochemical and kinetic analyses of NS5B RNA-dependent RNA polymerase of the hepatitis C virus". Virology, Article No. VY989311, Vo. 249, 1998, pp. 108-118.

Lohmann, V., et al., "Biochemical Properties of hepatitis C virus NS5B RNA-dependent RNA polymerase and identification of amino acid sequence motifs essential for enzymatic activity". Journal of Virology, Nov. 1997, Vo. 71, No. 11, pp. 8416-8428.

Love, R. A., et al., "The crystal structure of hepatitis C virus NS3 proteinase reveals a trypsin-like fold and a structural zinc binding site". Cell, vol. 87, 1996, pp. 331-342.

Luo, G., et al., "DeNovo initiation of RNA synthesis by the RNA-dependent RNA polymerase (NS5B) of hepatitis C virus". Journal of Virology, Jan. 2000, vol. 74, No. 2, pp. 851-863.

Mayer et al, "Solid-Phase Synthesis of Benzimidazoles"; Tetrahedron Letters 39 (1998) 6655-6658.

McKercher, G., et al., "Specific inhibitors of HCV polymerase identified using an NS5B with lower affinity for template/primer substrate". Nucleic Acids Research, 2004, vol. 32, No. 2, pp. 422-431.

Merlic, C.A. et al. "Benzannulation reactions of Fischer carbene compleses for the synthesis of indolocarbozoles" Tetrahedron, vol. 57, No. 24, pp. 5199-5212, 2001.

Miller, J.A. et al, "Preparation of Unsymmetrical Biaryls via Ni-or Pd-Catalyzed Coupling of Aryl chlorides with Arylzincs". Tetrahdron Letters, vol. 39 (36), 1998, pp. 6441-6444.

Minato, Akio et al, "Palladium-Phosphine Complex Catalyzed Cross-Coupling Reaction of 1-Methyl-2-pyrrolyl-magnesium Bromide and -zinc chloride with organic halides" Tetrahedron Letters, vol. 22, No. 52, 1981 p. 5319.

Miyaura, N. et al. "Palladium Catalyzed Cross-Coupling Reactions of Organoboron Compounds", Chem. Rev. 1995, vol. 95, pp. 2457-2483.

Murata, M.; Oyama, T.; Watanabe, S., Masuda, Y. "Palladium-Catalyzed Borylation of Aryl Halides or Triflates with Dialkoxyborne: A Novel and Facile Synthetic Route to Arylboronates;" J. Org. Chem. 2000, 65, 164.

Negishi, S. Baba, "Novel Stereoselective Alkenyl-Aryl Coupling via Nickel-catalysed Reaction of Alkenylalanes with Aryl Halides;" J. Chem. Soc. Chem. Communications, 1976, 596-597.

Oh, J-W, et al., "A recombinant hepatitis C virus RNA-dependent RNA polymerase capable of copying the full-length viral RNA". Journal of Virology, Sep. 1999, Vo. 73, No. 9, pp. 7694-7702.

Perandones, F. et al; Synthesis of imidazol[4,5-b]pyridines from aminoimidazolecarbaldehydes, J. heterocyc. Chem. vol. 34, pp. 107-112, 1997.

Qin, W. et al., "Mutational analysis of the structure and function of hepatitis C virus RNA-dependent RNA polymerase". American Assoc. for the Study of Liver Diseases. Hepatology, vol. 33, No. 3, 2001, pp. 728,737.

Reed, K.E., et al., "Phosphorylation of the hepatitis C virus NS5A protein in vitro and in vivo: properties of the NS5A-associated kinase". Journal of Virology, Oct. 1997, Vol. 71, No. 10, pp. 7187-7197.

Reed, K.E.; Rice, C.M.; "Overview of Hepatitis C Virus Genome Structure, Polyprotein Processing, and Protein Properties;" 1999; Curr. Top. Microbiol. Immunol. 242: pp. 55-84.

Reichard, O. et al, "Therapy of Hepatitis C: Alpha Interferon and Ribavirin," 1997 Hepatology 26; pp. 108S-111S.

Rice, C.M.; 1996; "Flavivindae: the viruses and their replication"; pp. 931-960 in Fields Virology; Fields, B.N.; Knipe, D.M.; Howley, P.M. (eds.); Lippincott-Raven Publishers, Philadelphia, PA.

Rorrer, L.C. et al. "Convenient New Route to Tetradentate and Pentadentate Macrocyclic Tetraamide Ligands", Organic Letters, 1999, vol. 1, No. 8, pp. 1157-1159.

Roth, H. J., et al; "Synthesis of Indole and Carbazole Derivatives by Condensation of Alpha-hydroxyketones and Aromatic Amines"; Archiv der Pharmazie und Berichte der Deutschen Pharmazeutischen Gesellschaft (1972), 305(3), pp. 159-171 (XP-002233858).

Sakamoto, T., et al, "Indolylzinc Iodides by Oxidative addition of activ zinc to Iodoindoles" Tetrahedron Letters, vol. 34, No. 37, 1993, p. 5955.

Sarisky, R.T. "Non-nucleoside inhibitors of the HCV polymerase". Journal of Antimicrobial Chemotherapy, 2004, 54, pp. 14-16.

Sarrazin, C., et al., "SCH 503034, a Novel hepatitis C virus protease inhibitor, plus pegylated inteferon a-2b for genotype 1 nonresponders". Gastroenterolgy, 2007, 132, pp. 1270-1278.

Simons, J. N., et al., "Identification of two flavivirus-like genomes in the GB hepatitis agent". Proc. Natl, Acad. Sci, Medical Sciences, Vo. 92, Apr. 1995, pp. 3401-3405.

Stanforth, S.P. "Catalytic Cross-coupling Reactions in Biaryl Synthesis" Tetrahedron, vol. 54(3-4), 1998, pp. 263-303.

Sun, X-L. et al., "De Novo RNA synthesis catalyzed by HCV RNA-dependent RNA polymerase". Biochemical and Biophysical Research Communications, vol. 268, 2000, pp. 798-803.

Takehide, N. et al; "Benzo-Heterocyclic Derivative"; Patent Abstracts of Japan; Publication No. 09124632 A; May 13, 1997.

Tomei, L., et al., "Biochemical characterization of a hepatitis C virus RNA-dependent RNA polymerse mutant lacking the C-terminal hydrophobic sequence". Journal of General Virology, 2000, 81, pp. 759,767.

Watanabe, T. et al, "Synthesis of sterically hindered blaryis via the palladium-catalyzed cross-coupling reaction of aryliboronic acids of their esters with haloarenes" Synlett, vol. 3, pp. 207-210, 1992.

Wu et al; "One-pot' nitro reduction-cyclisation solid phase route to benzimidazoles"; Tetrahedron Letters 41 (2000) 9871-9874.

Yamashita, T., et al., "RNA-dependent RNA polymerase activity of the soluble recombinant hepatitis C virus NS5B protein truncated at the C-terminal region". The Journal of Biological Chemistry, vol. 273, No. 25, Jun. 1999, pp. 15479-15486.

Yanagi, M., et al., "Transcripts from a single full-length cDNA clone of hepatitis C virus are infectious when directly transfected into the liver of a chimpanzee". PNAS, Vo. 94, Aug. 1997, pp. 8738-8743.

Youngdale, G. A. et al; "Synthesis and Antiinflammatory Activity of 5-Substituted 2,3-bis(p-methoxyphenyl) indoles"; J Med Chem (1969) 12, pp. 948-949 (XP-002233859).

Yuan, Z-H, et al., "Expression, purfication, and partial characterization of HCV RNA polymerase". Biochemical and Biophysical Research Communications, vol. 232, 1997, pp. 231-235.

Zhang, H-C., et al: "Efficient synthesis of 3-substituted 2-arylindoles via Suzuki coupling reactions in the solid phase"; Tetrahedron Letters, 42, 2001, pp. 4751-4754.

Zhang, J-H, et al., "A simple statistical parameter for use in evaluation and validation of high throughput screening assays". Journal of Biomolecular Screening, vol. 4, Nov. 1999, pp. 67-73.

Zhong, W., et al., "De Novo initiation of RNA synthesis by hepatitis C virus nonstructural protein 5B polymerase". Journal of Virology, Feb. 2000, Vo. 74, No. 4, pp. 2017-2022.

Zhong, W., et al., "Template/primer requirements and single nucleotide incorporation by hepatitis C virus nonstructural protein 5B polymerase". Journal of Virology, Oct. 2000, vol. 74, No. 19, pp. 9134-9143.

Afdhal, N, O'Brien C, Godofsky E, et al. Valpicitabine (NM283), alone or with PEG-interferon, compared to PEG interferon/ribavirin (PEGIFN/RBV) retreatment in patients with HCV-1 infection and prior non-response to PEBIFN/RBV: One-year results. Presented at the 42nd annual EASL meeting, Apr. 11-15, 2007, Barcelona, Spain.

Ago, H., et al., "Crystal structure of the RNA-dependent RNA polymerase of hepatitis C virus". Structure, 1999, V.7, No. 11, Research Article, pp.1417-1426.

Amat, Mercedes, et al, "An Efficient Synthesis of 2-(2-Pyridyl)indoles by Palladium (0)-catalyzed heteroarylation", Tetrahedron Letters, vol. 34, No. 31, 1993, p. 5005.

Baba et al.; "A Novel Stereospecific Alkenyl'Alkeny Cross-Coupling by a Palladium or Nickel-Catalyzed Reaction of Alkenylalanes with Alkenyl Halides" J. Am. Chem. Soc., 1976, 98, 6729- 6731.

Bartenschlager, R.,et al., "Nonstructural protein 3 of the hepatitis C virus encodes a serine-type proteinase required for cleavage at the NS3/4 and NS4/5 junctions". Journal of Virology, Jul. 1993, pp. 3835-3844.

Beaulieu et al. "Non-nucleoside inhibitors of the hepatitis C virus NS5B polymerase: discovery and preliminary SAR of benzimidazole derivatives." Bioorganic and Medicinal Chemistry Letters, 14 (2004) 119-124.

Beaulieu, P.L. et al; "Therapies for Hepatitis C Infection: Targeting the Non-Structural Proteins of HCV"; Curr. Med. Chem.-Anti-Infective Agents, 2002, vol. 1, No. 2, pp. 1-14.

Behrens, S-E., et al., "Identification and properties of the RNA-dependent RNA polymerase of hepatitis C virus". The EMBO Journal, vol. 15, No. 1, 1996, pp. 12-22.

Bressanellli, S., et al., "Crystal structure of the RNA-dependent RNA polymerase of hepatitis C virus". PNAS, Nov. 1999, Vo. 96, No. 23. pp. 13034-13039.

Bukh, J. et al., "Toward a surrogate model for hepatitis C virus: an infectious molecular clone of the GB virus-B hepatitis agent" Virology, vol. 262, 1999, pp. 470-478.

CA Abstract, CA 123: 33085, 1995.

CA Abstract, CA 126: 305540, 1997.

Carroll, S. S., et al., "Only a small fraction of purified hepatitis C RNA-dependent RNA polymerase is catalytically compentent: implications for viral replication and in vitro assays". Biochemistry, 2000, 39, pp. 8243-8249.

CAS Registry No. 115577-24-7 Registry Copyright 2001 ACS.

CAS Registry No. 214150-90-0 Registry Copyright 2001 ACS.

CAS Registry No. 214150-93-3 Registry Copyright 2001 ACS.

CAS Registry No. 66315-47-7 Registry Copyright 2001 ACS.

CAS Registry No. 66315-51-3 Registry Copyright 2001 ACS.

CAS Registry No. 66315-52-4 Registry Copyright 2001 ACS.

CAS Registry No. 66630-73-7 Registry Copyright 2001 ACS.

Chemical Abstract for DE 2642877: CA1977:453062.

Chemical Abstract for EP50957: CA1982:509865.

Chemical Abstract for EP73663: CA 1983:505247.

Chemical Abstract for WO 2000006556 A1: CA2000:98534.

Chemical Abstract for WO 2000026202 A1: CA2000:314687.

Chemical Abstract for WO 2000027846 A2: CA2000:335410.

Chemical Abstract for WO 2001/047883: CA2001:489367.

Chemical Abstract for WO 2001/087885: CA2001:851160.

Chemical Abstract for WO 9632379: CA 1996:746234.

Chemical Abstract for WO 9808847 A1: CA1998163594.

Chemical Abstract for WO 9829408 A1: CA1998:485053.

Chemical Abstract: CA 128:275074 for JP 10-067682.

Chemical Abstract: CA 129:45274 for JP 10 114654.

Chemical Abstract: CA 134:340435 for JP 2001 122855.

Chemical Abstract: CA 1968:418961.

Chemical Abstract: CA 1969:68209.

Chemical Abstract: CA 1986:514976.

Chemical Abstract: CA 1987:458985.

Chemical Abstract: CA 1990:234572.

Chemical Abstract: CA 384846-70-2.

Danieli, B. et al. "Application of the PD-catalyzed hetroarylation to the synthesis of 5-(indol2'-yl)pyridin-2-one and 5-(indol-2'yl) pyran-2-one" Tetrahedron, vol. 54, No. 46, 1998, p. 14081.

DeFrancesco, R., et al., "RNA-dependent RNA polymerase of hepatitis C virus". Methods in Enzymology, vol. 275, 1998, pp. 58-67.

Deutsch, M. et al; "Old and emerging therapies in chronic hepatitis C: an update;" 2008, J. of Viral Hepatitis, 15, p. 2-11.

Erhardt et al, "Safety, Pharmacokinetics and Antiviral effects of Boehringer Ingelheim BILB 1941, a Novel HCV RNA Polymerase, After 5 days Oral treatment in Patients with Chronic Hepatitis C", Poster from EASL 42nd Mtg. of Euruopean Association for the Study of Liver Diseases, Barcelona, Spain Apr. 11-15, 2007.

Ferrari, E., et al., "Characterization of soluble hepatitis C virus RNA-dependent RNA polymerase expressed in *Escherichia coli*". Journal of Virology, 1990, vol. 73, No. 2., pp. 1649-1654.

Fuerstner, A. et al; "Titanium-Induced Zipper Reactions"; Angewandte Chemie, International Edition in English (1995), 34(6), pgs 678-681 (XP-002233857).

Gale, M.J. et al., "Evidence that hepatitus C virus resistance to interferon is mediated through repression of the PKR protein kinase by the nonstructural 5A protein". Virology, 230, 1997, Article No. VY978493, pp. 217-227.

Grakoui, A., et al., "A second hepatitis C virus-encoded proteinase". Proc. Natl. Acad. Sci, USA, vol. 90, Nov. 1993, Biochemistry, pp. 10583-10587.

Grakoui, A., et al., "Expression and identification of hepatitis C virus polyprotein cleavage products". Journal of Virology, 193, vol. 67, No. 3, pp. 1385-1395.

Hashimoto, et al., WO 2001047883; CA 135:76874,2001.

* cited by examiner

US 7,838,537 B2

VIRAL POLYMERASE INHIBITORS

RELATED APPLICATIONS

This application is a Divisional Application of U.S. Ser. No. 11/405,144, filed Apr. 17, 2006, which is a Continuation of U.S. application Ser. No. 10/755,544, filed Jan. 12, 2004, for which benefit of U.S. Provisional Application Ser. No. 60/441,674, filed on Jan. 22, 2003, is hereby claimed and said application is herein incorporated by reference in its entirety.

TECHNICAL FIELD OF THE INVENTION

The invention relates to inhibitors of RNA dependent RNA polymerases, particularly those viral polymerases within the Flaviviridae family, more particularly to HCV polymerase.

BACKGROUND OF THE INVENTION

About 30,000 new cases of hepatitis C virus (HCV) infection are estimated to occur in the United States each year (Kolykhalov, A. A.; Mihalik, K.; Feinstone, S. M.; Rice, C. M.; 2000; *J. Virol.* 74: 2046-2051). HCV is not easily cleared by the hosts' immunological defenses; as many as 85% of the people infected with HCV become chronically infected. Many of these persistent infections result in chronic liver disease, including cirrhosis and hepatocellular carcinoma (Hoofnagle, J. H.; 1997; *Hepatology* 26: 15S-20S*). There are an estimated 170 million HCV carriers world-wide, and HCV-associated end-stage liver disease is now the leading cause of liver transplantation. In the United States alone, hepatitis C is responsible for 8,000 to 10,000 deaths annually. Without effective intervention, the number is expected to triple in the next 10 to 20 years. There is no vaccine to prevent HCV infection. Prolonged treatment of chronically infected patients with interferon or interferon and ribavirin is the only currently approved therapy, but it achieves a sustained response in fewer than 50% of cases (Lindsay, K. L.; 1997; *Hepatology* 26: 71S-77S*, and Reichard, O.; Schvarcz, R.; Weiland, O.; 1997 *Hepatology* 26: 108S-111S*).

HCV belongs to the family Flaviviridae, genus *hepacivirus*, which comprises three genera of small enveloped positive-strand RNA viruses (Rice, C. M.; 1996; "Flaviviridae: the viruses and their replication"; pp. 931-960 in *Fields Virology*; Fields, B. N.; Knipe, D. M.; Howley, P. M. (eds.); Lippincott-Raven Publishers, Philadelphia Pa.*). The 9.6 kb genome of HCV consists of a long open reading frame (ORF) flanked by 5' and 3' non-translated regions (NTR's). The HCV 5' NTR is 341 nucleotides in length and functions as an internal ribosome entry site for cap-independent translation initiation (Lemon, S. H.; Honda, M.; 1997; *Semin. Virol.* 8: 274-288). The HCV polyprotein is cleaved co- and post-translationally into at least 10 individual polypeptides (Reed, K. E.; Rice, C. M.; 1999; *Curr. Top. Microbiol. Immunol.* 242: 55-84*). The structural proteins result from signal peptidases in the N-terminal portion of the polyprotein. Two viral proteases mediate downstream cleavages to produce non-structural (NS) proteins that function as components of the HCV RNA replicase. The NS2-3 protease spans the C-terminal half of the NS2 and the N-terminal one-third of NS3 and catalyses cis cleavage of the NS2/3 site. The same portion of NS3 also encodes the catalytic domain of the NS3-4A serine protease that cleaves at four downstream sites. The C-terminal two-thirds of NS3 is highly conserved amongst HCV isolates, with RNA-binding, RNA-stimulated NTPase, and RNA unwinding activities. Although NS4B and the NS5A phosphoprotein are also likely components of the replicase, their specific roles are unknown. The C-terminal polyprotein cleavage product, NS5B, is the elongation subunit of the HCV replicase possessing RNA-dependent RNA polymerase (RdRp) activity (Behrens, S. E.; Tomei, L.; DeFrancesco, R.; 1996; *EMBO J.* 15: 12-22*; and Lohmann, V.; Körner, F.; Herian, U.; Bartenschlager, R.; 1997; *J. Virol.* 71: 8416-8428*). It has been recently demonstrated that mutations destroying NS5B activity abolish infectivity of RNA in a chimp model (Kolykhalov, A. A.; Mihalik, K.; Feinstone, S. M.; Rice, C. M.; 2000; *J. Virol.* 74: 2046-2051*).

The development of new and specific anti-HCV treatments is a high priority, and virus-specific functions essential for replication are the most attractive targets for drug development. The absence of RNA dependent RNA polymerases in mammals, and the fact that this enzyme appears to be essential to viral replication, would suggest that the NS5B polymerase is an ideal target for anti-HCV therapeutics.

WO 00/06529, WO 00/13708, WO 00/10573, WO 00/18231, WO 01/47883, WO 01/85172, WO 02/04425, WO 03/010140 and WO 03/010141 report inhibitors of NS5B proposed for treatment of HCV.

SUMMARY OF THE INVENTION

It is therefore an object of the invention to provide a novel series of compounds having inhibitory activity against HCV polymerase.

Further objects of this invention arise for the one skilled in the art from the following description and the examples.

In a first aspect of the invention, there is provided an isomer, enantiomer, diastereoisomer or tautomer of a compound, represented by formula I:

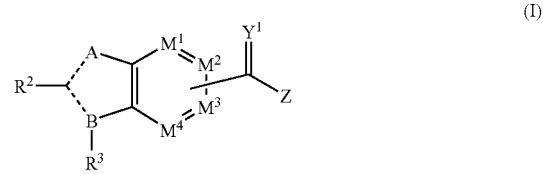

(I)

wherein
----- represents either a single or a double bond;
B is —N— and A is =CR$^1$— or =N—; or
B is =C— and A is O, S or NR$^1$;
R$^1$ is selected from the group consisting of: H, (C$_{1-6}$)alkyl optionally substituted with:
  halogen, OR$^{11}$, SR$^{11}$ or N(R$^{12}$)$_2$, wherein R$^{11}$ and each R$^{12}$ is independently H, (C$_{1-6}$)alkyl, (C$_{3-7}$)cycloalkyl, (C$_{1-6}$)alkyl-(C$_{3-7}$)cycloalkyl, (C$_{1-6}$)alkyl-aryl or (C$_{1-6}$)alkyl-Het, said aryl or Het optionally substituted with R$^{160}$; or both R$^{12}$ are covalently bonded together and to the nitrogen to which they are both attached to form a 5, 6 or 7-membered saturated heterocycle;
the group —C(=Y$^1$)—Z is covalently linked to either M$^2$ or M$^3$,
M$^1$ is CR$^{4a}$,
M$^2$ or M$^3$, when not linked to —C(=Y$^1$)—Z, is CR$^5$,
M$^4$ is CR$^{4b}$,
and in addition one or two of the groups selected from M$^1$, M$^2$, M$^3$ and M$^4$ may also be N, with the proviso that the group M$^2$ or M$^3$ to which —C(=Y$^1$)—Z is linked is a C-atom,
Y$^1$ is O or S;

Z is defined as $NR^{N2}$—$SO_2$—$R^C$ or $NR^{N3}$—$SO_2$—$N(R^{N2})$ $R^{N1}$, wherein $R^C$, $R^{N1}$ or any heterocycle formed by $R^{N1}$ and $R^{N2}$ is optionally substituted with $R^{60}$;

$R^2$ is selected from: halogen or $R^{21}$, wherein $R^{21}$ is aryl or Het, said $R^{21}$ is optionally substituted with $R^{150}$;

$R^3$ is selected from $(C_{1-6})$alkyl, $(C_{3-7})$cycloalkyl, $(C_{1-3})$alkyl-$(C_{3-7})$cycloalkyl, $(C_{5-7})$cycloalkenyl, $(C_{1-3})$alkyl-$(C_{5-7})$cycloalkenyl, $(C_{6-10})$bicycloalkyl, $(C_{1-3})$alkyl-$(C_{6-10})$bicycloalkyl, $(C_{6-10})$bicycloalkenyl, $(C_{1-3})$alkyl-$(C_{6-10})$bicycloalkenyl, HCy or $(C_{1-3})$alkyl-HCy, wherein HCy is a saturated or unsaturated 4 to 7-membered heterocyclic group with 1 to 3 heteroatoms selected from O, S and N;

said alkyl, cycloalkyl, cycloalkenyl, bicycloalkyl, bicycloalkenyl, HCy and alkyl-HCy being optionally substituted with from 1 to 4 substituents selected from:
  a) halogen;
  b) $(C_{1-6})$alkyl optionally substituted with:
    1 to 3 substituents selected from halogen;
    $OR^{31}$ or $SR^{31}$ wherein $R^{31}$ is H, $(C_{1-6})$alkyl, $(C_{3-7})$ cycloalkyl or $(C_{1-3})$alkyl-$(C_{3-7})$cycloalkyl; or
    $N(R^{32})_2$ wherein each $R^{32}$ is independently H, $(C_{1-6})$ alkyl, $(C_{3-7})$cycloalkyl or $(C_{1-3})$alkyl-$(C_{3-7})$cycloalkyl; or both $R^{32}$ are covalently bonded together and to the nitrogen to which they are attached to form a 5, 6 or 7-membered saturated heterocycle;
  c) $OR^{33}$ or $SR^{33}$ wherein $R^{33}$ is H, $(C_{1-6})$alkyl, $(C_{3-7})$ cycloalkyl or $(C_{1-3})$alkyl-$(C_{3-7})$cycloalkyl;
  d) $N(R^{35})_2$ wherein each $R^{35}$ is independently H, $(C_{1-6})$ alkyl, $(C_{3-7})$cycloalkyl or $(C_{1-3})$alkyl-$(C_{3-7})$cycloalkyl; or both $R^{35}$ are covalently bonded together and to the nitrogen to which they are attached to form a 5, 6 or 7-membered saturated heterocycle;

$R^{4a}$, $R^{4b}$, $R^5$ each are independently H or defined as $R^{150}$;

$R^{60}$ is defined as 1 to 4 substituents independently selected from:
  1 to 3 substituents selected from halogen;
  one of each substituent selected from: $OPO_3H$, $NO_2$, cyano, azido, $C(=NH)NH_2$, $C(=NH)NH(C_{1-6})$alkyl or $C(=NH)NHCO(C_{1-6})$alkyl, $SO_3H$; and
  1 to 3 substituents selected from:
    a) $(C_{1-6})$ alkyl, $(C_{3-7})$cycloalkyl, $(C_{3-7})$ spirocycloalkyl optionally containing 1 or 2 heteroatoms selected from N, O and S; $(C_{2-6})$alkenyl, $(C_{2-8})$alkynyl, $(C_{1-6})$alkyl-$(C_{3-7})$cycloalkyl, all of which optionally being substituted with $R^{150}$;
    b) $OR^O$;
    c) $OC(O)R^O$;
    d) $SR^O$, $SO_2R^C$, $SO_2N(R^{N2})R^{N1}$, $SO_2N(R^{N2})C(O)R^C$, $CONR^{N3}SO_2N(R^{N2})R^{N1}$, or $CONR^{N2}SO_2R^C$;
    e) $N(R^{N2})R^{N1}$ $N(R^{N2})COOR^C$, $N(R^{N2})SO_2R^C$ or $N(R^{N1})OR^O$;
    f) $N(R^{N2})COR^C$;
    g) $N(R^{N3})CON(R^{N2})R^{N1}$;
    h) $N(R^{N3})COCOR^C$, $N(R^{N3})COCOOR^O$, $N(R^{N3})COCON(R^{N2})OR^O$, or $N(R^{N3})COCON(R^{N2})R^{N1}$;
    i) $COR^O$;
    j) $COOR^O$;
    k) $CON(R^{N2})R^{N1}$;
    l) aryl, Het, $(C_{1-4})$alkyl-aryl or $(C_{1-4})$alkyl-Het, all of which optionally being substituted with $R^{150}$;
    wherein said $R^{N1}$, $R^C$ and/or $R^O$ are optionally substituted with $R^{150}$ as defined, $R^{150}$ is defined as 1 to 4 substituents independently selected from:
  1 to 3 substituents selected from halogen;
  one of each substituent selected from: $OPO_3H$, $NO_2$, cyano, azido, $SO_3H$ $C(=NH)NH_2$, $C(=NH)NH(C_{1-6})$alkyl or $C(=NH)NHCO(C_{1-6})$alkyl; and
  1 to 3 substituents selected from:
    a) $(C_{1-6})$ alkyl, $(C_{3-7})$cycloalkyl, $(C_{3-7})$spirocycloalkyl optionally containing 1 or 2 heteroatoms selected from N, O and S; $(C_{2-6})$alkenyl, $(C_{2-8})$alkynyl, $(C_{1-3})$ alkyl-$(C_{3-7})$cycloalkyl, all of which optionally substituted with $R^{160}$;
    b) $OR^O$;
    c) $OC(O)R^O$;
    d) $SR^O$, $SO_2R^C$, $SO_2N(R^{N2})R^{N1}$ or $SO_2N(R^{N2})C(O)R^C$;
    e) $N(R^{N2})R^{N1}$, $N(R^{N2})COOR^C$, $N(R^{N2})SO_2R^C$ or $N(R^{N1})OR^O$;
    f) $N(R^{N2})COR^C$;
    g) $N(R^{N3})CON(R^{N2})R^{N1}$;
    h) $N(R^{N3})COCOR^C$, $N(R^{N3})COCOOR^O$, $N(R^{N3})COCON(R^{N2})OH$, $N(R^{N3})COCON(R^{N2})O(C_{1-4})$alkyl or $N(R^{N3})COCON(R^{N2})R^{N1}$;
    i) $COR^O$;
    j) $COOR^O$;
    k) tetrazole, triazole, $CONR^{N2}SO_2R^C$, $CONR^{N3}$—$SO_2N(R^{N2})R^{N1}$ or $CON(R^{N2})R^{N1}$;
    wherein said $R^{N1}$, $R^C$ and/or $R^O$ are optionally substituted with $R^{160}$ as defined;

$R^{160}$ is defined as 1, 2 or 3 substituents independently selected from:
  1, 2 or 3 fluorine substituents; and
  one of each substituent selected from tetrazole, triazole, chlorine, bromine, iodine, CN, nitro, $(C_{1-4})$alkyl, $OCF_3$, $SCF_3$, $CF_3$, $COOR^{161}$, $SO_3H$, $SR^{161}$, $SO_2R^{163}$, $OR^{161}$, $N(R^{162})_2$, $SO_2N(R^{162})_2$, $SO_2NR^{162}COR^{162}$, $NR^{162}SO_2R^{163}$, —$NR^{161}$—CO—$COOR^{161}$, —$NR^{161}$—CO—$CO(NR^{162})_2$, —$CONR^{161}SO_2R^C$, $CONR^{161}$—$SO_2N(R^{162})_2$ or $SO_2$—$NR^{161}$—$COR^C$, $NR^{162}COR^{162}$ or $CON(R^{162})_2$, wherein $R^{161}$, $R^{163}$ and each $R^{162}$ is independently $(C_{1-4})$alkyl, $(C_{3-7})$cycloalkyl or $(C_{1-3})$alkyl-$(C_{3-7})$cycloalkyl; and $R^{161}$ and each $R^{162}$ may each independently also be H; or both $R^{162}$ are covalently bonded together and to the nitrogen to which they are attached to form a 5, 6 or 7-membered saturated heterocycle;

$R^O$, $R^C$ are independently defined as $(C_{1-6})$alkyl, $(C_{3-7})$cycloalkyl, $(C_{1-4})$alkyl-$(C_{3-7})$cycloalkyl, $(C_{2-6})$alkenyl, aryl, Het, $(C_{1-4})$alkyl-aryl, or $(C_{1-4})$alkyl-Het; or $R^O$ is also optionally defined as H.

$R^{N1}$ is H, $(C_{1-6})$alkyl, $(C_{3-7})$cycloalkyl, $(C_{1-4})$alkyl-$(C_{3-7})$cycloalkyl, $(C_{2-6})$alkenyl, aryl, Het, $(C_{1-4})$alkyl-aryl, $(C_{1-4})$alkyl-Het; and $R^{N2}$, $R^{N3}$, $R^{N4}$ are independently H, $CH_3$, $(C_{2-6})$alkyl, $(C_{3-6})$cycloalkyl, $(C_{1-4})$alkyl-$(C_{3-6})$cycloalkyl; all of which being optionally substituted with halogen, carboxy or $(C_{1-6})$alkoxycarbonyl; and/or wherein said alkyl, cycloalkyl or alkylcycloalkyl is optionally substituted with hydroxy, $(C_{1-6})$alkyl, $(C_{1-6})$alkoxy, amino, —$NH(C_{1-4})$alkyl and/or —$N((C_{1-4})$alkyl$)_2$; or in the case
  a) of a group $N(R^{N2})R^{N1}$ the substituents $R^{N2}$ and $R^{N1}$; or
  b) of a group $NR^{N3}$—$N(R^{N2})R^{N1}$ the substituents $R^{N3}$ and $R^{N1}$, or $R^{N2}$ and $R^{N1}$; may be covalently bonded together to form a 4-, 5-, 6- or 7-membered saturated or unsaturated N-containing heterocycle or a 8-, 9-, 10- or 11-membered N-containing heterobicycle, each optionally having additionally from 1 to 3 heteroatoms selected from O, N, and S, wherein said heterocycle or heterobicycle is optionally substituted as defined;

wherein Het is defined as a 4-, 5-, 6- or 7-membered heterocycle having 1 to 4 heteroatoms selected from O, N and S, or a 8-, 9-, 10- or 11-membered heterobicycle having 1 to 5 heteroatoms selected from O, N and S;

or a salt thereof.

Included within the scope of this invention are compounds of the formula (I) as described hereinbefore, to which a "detectable label", "affinity tag" or "photoreactive group" is linked.

The compounds according to this invention generally show an inhibitory activity against HCV polymerase. In particular compounds according to this invention inhibit RNA synthesis by the RNA dependent RNA polymerase of HCV, especially of the enzyme NS5B encoded by HCV. Furthermore, compounds being active in cell culture are provided. A further advantage of compounds provided by this invention is their low to very low or even non-significant activity against other polymerases.

In a second aspect of the invention, there is provided a use of a compound of formula I according to this invention, or a pharmaceutically acceptable salt thereof, as an HCV polymerase inhibitor.

In a third aspect of the invention, there is provided a use of a compound of the formula I according to this invention, or a pharmaceutically acceptable salt thereof, as an inhibitor of RNA dependent RNA polymerase activity of the enzyme NS5B, encoded by HCV.

In a fourth aspect of the invention, there is provided a use of a compound of the formula I according to this invention, or a pharmaceutically acceptable salt thereof, as an inhibitor of HCV replication.

In a fifth aspect of the invention, there is provided a method of treating or preventing HCV infection in a mammal, comprising administering to the mammal an effective amount of a compound of formula I according to this invention, or a pharmaceutically acceptable salt thereof.

In a sixth aspect of the invention, there is provided a method of treating or preventing HCV infection in a mammal, comprising administering to the mammal an effective amount of a compound of formula I, or a pharmaceutically acceptable salt thereof in combination with another antiviral agent.

In a seventh aspect of the invention, there is provided a pharmaceutical composition for the treatment or prevention of HCV infection, comprising an effective amount of a compound of formula I according to this invention, or a pharmaceutically acceptable salt thereof, and a pharmaceutically acceptable carrier.

According to a further specific embodiment, the pharmaceutical composition of this invention comprises a therapeutically effective amount of one or more antiviral agents. Examples of antiviral agents include, ribavirin and amantadine.

According to a further specific embodiment, the pharmaceutical composition of this invention comprises an other anti-HCV agent as an antiviral agent.

According to a more specific embodiment, the pharmaceutical composition of this invention comprises an additional immunomodulatory agent as an other anti-HCV agent. Examples of additional immunomodulatory agents include but are not limited to, α-, β-, δ-, γ-, tau- and ω-interferons.

According to another more specific embodiment, the pharmaceutical composition of this invention comprises another inhibitor of HCV polymerase as an other anti-HCV agent.

According to another more specific embodiment, the pharmaceutical composition of this invention comprises an inhibitor of HCV NS3 protease as an other anti-HCV agent.

According to yet another more specific embodiment, the pharmaceutical composition of this invention comprises an inhibitor of another target in the HCV life cycle as an other anti-HCV agent. Examples of such other targets are HCV helicase, HCV NS2/3 protease or HCV IRES.

In an eighth aspect of the invention, there is provided a use of a compound of formula I according to this invention, or of a pharmaceutically acceptable salt thereof, for the manufacture of a medicament for the treatment and/or the prevention of a Flaviviridae viral infection, preferably an HCV infection.

DETAILED DESCRIPTION OF THE INVENTION

Definitions

The following definitions apply unless otherwise noted:

As used herein, the term $(C_{1-n})$ alkyl or $C_{1-n}$alkyl, wherein n is an integer, either alone or in combination with another radical, are intended to mean acyclic straight or branched chain alkyl radicals containing 1 to n carbon atoms respectively. Examples of such radicals include methyl, ethyl, n-propyl, 1-methylethyl (i-propyl), n-butyl, 1-methylpropyl, 2-methylpropyl, 1,1-dimethylethyl (tert.-butyl), n-pentyl, etc. In the following the term Me denotes a methyl group.

If an alkyl group is substituted by halogen, it is preferably mono-, di- or trisubstituted with fluorine or monosubstituted by chlorine or bromine. Preferred alkyl-groups which are trisubstituted with fluorine have a terminal $CF_3$ group.

As used herein, the term $(C_{2-n})$ alkenyl, wherein n is an integer, either alone or in combination with another radical, is intended to mean an unsaturated, acyclic straight chain radical containing two to n carbon atoms, at least two of which are bonded to each other by a double bond. Examples of such radicals are ethenyl (vinyl), 1-propenyl, 2-propenyl, 1-butenyl, etc.

As used herein, the term $(C_{2-n})$ alkynyl, wherein n is an integer, either alone or in combination with another group, is intended to mean an unsaturated, acyclic straight chain alkynyl radical containing 2 to n carbon atoms, at least two of which are bonded to each other by a triple bond. Examples of such radicals are ethynyl, 1-propynyl, 2-propynyl, etc.

As used herein, the term $(C_{3-n})$cycloalkyl, wherein n is an integer, either alone or in combination with another radical, means a cycloalkyl radical containing from three to n carbon atoms and includes cyclopropyl, cyclobutyl, cyclopentyl, cyclohexyl and cycloheptyl.

As used herein, the term $(C_{5-n})$cycloalkenyl, wherein n is an integer, either alone or in combination with another radical, means an unsaturated cyclic radical containing five to n carbon atoms. Examples are cyclopentenyl and cyclohexenyl.

As used herein the term $(C_{1-n})$alkyl-$(C_{3-m})$cycloalkyl, wherein n and m are integers, either alone or in combination with another radical, means a branched or straight chain alkyl radical having 1 to n C-atoms to which a cycloalkyl radical containing from three to m C-atoms is covalently bonded. Preferably the alkyl radical is a straight chain and the cycloalkyl radical is linked to its terminal C-atom. Examples of $(C_{1-3})$alkyl-$(C_{3-6})$cycloalkyl include cyclopropylmethyl, cyclobutylmethyl, cyclopentylmethyl, cyclohexylmethyl, 2-cyclopropylethyl, 2-cyclobutylethyl, 2-cyclopentylethyl, 2-cyclohexylethyl, 3-cyclopropylpropyl, 3-cyclobutylpropyl, 3-cyclopentylpropyl, 3-cyclohexylpropyl, etc.

As used herein, the terms alkyl-aryl, alkyl-HCy, alkyl-Hetaryl, alkyl-Het, etc. mean an alkyl radical to which an aryl, HCy, Hetaryl, Het group is bonded, respectively. Examples of $(C_{1-3})$alkyl-aryl are benzyl (phenylmethyl), phenylethyl and phenylpropyl.

As used herein, the term "carboxy protecting group" (CPG) defines protecting groups that can be used during synthetic transformation and are listed in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference.

A carboxyl group is usually protected as an ester that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

As used herein, the term "aryl" either alone or in combination with another radical means a 6- or 10-membered aryl, i.e. an aromatic radical containing six or ten carbon atoms, for example phenyl, 1-naphthyl or 2-naphthyl. The most preferred meaning of aryl is phenyl.

As used herein the term heteroatom means O, S or N.

As used herein, the term "heterocycle", either alone or in combination with another radical, means a monovalent radical derived by removal of a hydrogen from a five-, six-, or seven-membered saturated or unsaturated (including aromatic) heterocycle containing from one to four heteroatoms selected from nitrogen, oxygen and sulfur. Examples of such heterocycles include, but are not limited to, azetidine, pyrrolidine, tetrahydrofuran, thiazolidine, pyrrole, thiophene, hydantoin, diazepine, 1H-imidazole, isoxazole, thiazole, tetrazole, piperidine, piperazine, homopiperidine, homo-piperazine, 1,4-dioxane, 4-morpholine, 4-thiomorpholine, pyridine, pyridine-N-oxide or pyrimidine, or the following heterocycles:

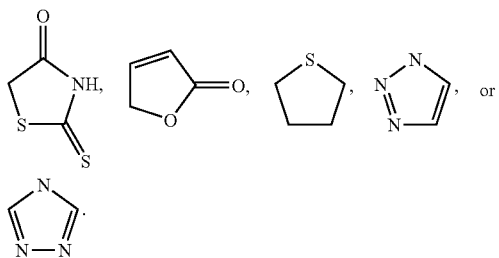

As used herein, the term "9- or 10-membered heterobicycle" or "heterobicycle" either alone or in combination with another radical, means a heterocycle as defined above fused to one or more other cycle, be it a heterocycle or any other cycle. Examples of such heterobicycles include, but are not limited to, indole, benzimidazole, thiazolo[4,5-b]-pyridine, quinoline, or coumarin, or the following:

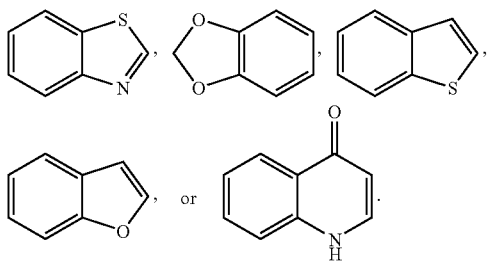

As used herein, the term "Het" defines a 4-, 5-, 6- or 7-membered heterocycle having 1 to 4 heteroatoms selected from O, N and S, which may be saturated, unsaturated or aromatic, or a 8-, 9-, 10- or 11-membered heterobicycle having 1 to 5 heteroatoms wherever possible, selected from O, N and S, which may be saturated, unsaturated or aromatic, unless specified otherwise.

As used herein, the term "HCy" defines a saturated or unsaturated 4-, 5-, 6- or 7-membered monocyclic heterocycle having 1 to 3 heteroatoms selected from O, N and S, unless specified otherwise.

As used herein, the term "Hetaryl" defines an aromatic 5- or 6-membered monocyclic heterocycle having 1 or 2 heteroatoms selected from O, N and S, or a 9- or 10-membered aromatic heterobicycle having 1 to 4 heteroatoms selected from O, N, and S, unless specified otherwise.

As used herein, the term "halo" means a halogen atom and includes fluorine, chlorine, bromine and iodine.

As used herein, the term "OH" refers to a hydroxyl group. It is well known to one skilled in the art that hydroxyl groups may be substituted by functional group equivalents. Examples of such functional group equivalents that are contemplated by this invention include, but are not limited to, ethers, sulfhydryls, and primary, secondary or tertiary amines.

As used herein, the term "SH" refers to a sulfhydryl group. It is intended within the scope of the present invention that, whenever a "SH" or "SR" group is present, it can also be substituted by any other appropriate oxidation state such as $SOR$, $SO_2R$, or $SO_3R$.

It is intended that the term "substituted" when applied in conjunction with a radical having more than one moiety such as $C_{1-6}$alkyl-aryl, or $C_{1-6}$alkyl-Het, such substitution applies to both moieties i.e. both the alkyl and aryl or Het moieties can be substituted with the defined substituents.

As used herein, the term "COOH" refers to a carboxylic acid group. It is well known to one skilled in the art that carboxylic acid groups may be substituted by functional group equivalents. Examples of such functional group equivalents that are contemplated by this invention include, but are not limited to, esters, amides, imides, boronic acids, tetrazole, triazoles, N-acylsulfonyldiamides ($RCONHSO_2NR_2$), and acylsulfonamides ($RCONHSO_2R$).

As used herein, the term "functional group equivalent" is intended to mean an element or a substituted derivative thereof, that is replaceable by another element that has similar electronic, hybridization or bonding properties.

As used herein, the term "metal catalyst" is intended to mean a metal such as palladium (0) or palladium (2) for use in a cross-coupling reaction. Examples of such palladium catalysts include, but are not limited to, $Pd(PPh_3)_4$, Pd/C, $Pd(OAc)_2$, $PdCl_2$, and the like. Alternative metals that can catalyze cross-coupling reactions include, but are not limited to complexes of Ni, Rh, Ru and Ir, like for example: Ni$(acac)_2$, $Ni(OAc)_2$, or $NiCl_2$.

The term "detectable label" refers to any group that may be linked to the polymerase or to a compound of the present invention such that when the compound is associated with the polymerase target, such label allows recognition either directly or indirectly of the compound such that it can be detected, measured and quantified. Examples of such "labels" are intended to include, but are not limited to, fluorescent labels, chemiluminescent labels, colorimetric labels, enzymatic markers, radioactive isotopes and affinity tags such as biotin. Such labels are attached to the compound or to the polymerase by well known methods.

The term "affinity tag" means a ligand (that is linked to the polymerase or to a compound of the present invention) whose strong affinity for a receptor can be used to extract from a solution the entity to which the ligand is attached. Examples of such ligands include biotin or a derivative thereof, a histidine polypeptide, a polyarginine, an amylose sugar moiety or a defined epitope recognizable by a specific antibody. Such affinity tags are attached to the compound or to the polymerase by well-known methods.

The term "photoreactive group" means a group that is transformed, upon activation by light, from an inert group to a reactive species, such as a free radical. Examples of such groups include, but are not limited to, benzophenones, azides, and the like.

The term "salt thereof" means any acid and/or base addition salt of a compound according to the invention; preferably a pharmaceutically acceptable salt thereof.

The term "pharmaceutically acceptable salt" means a salt of a compound of formula (I) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19, which is hereby incorporated by reference in its entirety.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, sulfuric acid, sulfamic acid, nitric acid, phosphoric acid, and the like, and organic acids such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethane-sulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Antiviral agents include, for example, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals).

The term "other anti-HCV agent" as used herein means those agents that are effective for diminishing or preventing the progression of hepatitis C related symptoms of disease. Such agents can be selected from: immunomodulatory agents, inhibitors of HCV NS3 protease, other inhibitors of HCV polymerase or inhibitors of another target in the HCV life cycle.

The term "immunomodulatory agent" as used herein means those agents (compounds or biologicals) that are effective to enhance or potentiate the immune system response in a mammal. Immunomodulatory agents include, for example, class I interferons (such as $\alpha$-, $\beta$-, $\delta$- and omega interferons, tau-interferons, consensus interferons and asialo-interferons), class II interferons (such as $\gamma$-interferons) and pegylated interferons.

The term "inhibitor of HCV NS3 protease" as used herein means an agent (compound or biological) that is effective to inhibit the function of HCV NS3 protease in a mammal. Inhibitors of HCV NS3 protease include, for example, those compounds described in WO 99/07733, WO 99/07734, WO 00/09558, WO 00/09543, WO 00/59929 or WO 02/060926, the Boehringer Ingelheim clinical candidate identified as BILN 2061 and the Vertex pre-development candidate identified as VX-950. Particularly, compounds #2, 3, 5, 6, 8, 10, 11, 18, 19, 29, 30, 31, 32, 33, 37, 38, 55, 59, 71, 91, 103, 104, 105, 112, 113, 114, 115, 116, 120, 122, 123, 124, 125, 126 and 127 disclosed in the table of pages 224-226 in WO 02/060926, can be used in combination with the compounds of the present invention.

The term "other inhibitor of HCV polymerase" as used herein means an agent (compound or biological) that is effective to inhibit the function of HCV polymerase in a mammal, whereby this agent has a structure different from the compounds according to this invention and preferably binds to a site of the HCV polymerase different from the site targeted by the compounds according to this invention. Other inhibitors of HCV polymerase include non-nucleosides, for example, those compounds described in: WO 03/040112 (Rigel), WO 02/100846 A1 (Shire), WO 02/100851 A2 (Shire), WO 01/85172 A1 (GSK), WO 02/098424 A1 (GSK), WO 00/06529 (Merck), WO 02/06246 A1 (Merck), EP 1 256 628 A2 (Agouron). Furthermore other inhibitors of HCV polymerase also include nucleoside analogs, for example, those compounds described in: WO 01/90121 A2 (Idenix), WO 02/069903 A2 (Biocryst Pharmaceuticals Inc.), WO 02/057287 A2 (Merck/Isis) and WO 02/057425 A2 (Merck/Isis).

The term "inhibitor of another target in the HCV life cycle" as used herein means an agent (compound or biological) that is effective to inhibit the formation and/or replication of HCV in a mammal other than by inhibiting the RNA dependent RNA polymerase of HCV. This includes agents that interfere with either host or HCV viral mechanisms necessary for the formation and/or replication of HCV in a mammal. Inhibitors of another target in the HCV life cycle include, for example, agents that inhibit a target selected from a HCV helicase, HCV NS2/3 protease and HCV IRES. Specific examples of inhibitors of another target in the HCV life cycle include ISIS-14803 (ISIS Pharmaceuticals).

The term "HIV inhibitor" as used herein means an agents (compound or biological) that is effective to inhibit the formation and/or replication of HIV in a mammal. This includes agents that interfere with either host or viral mechanisms necessary for the formation and/or replication of HIV in a mammal. HIV inhibitors include, for example, nucleosidic inhibitors, non-nucleosidic inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type I. This includes both naturally and synthetically produced class I interferons. Examples of class I interferons include α-, β-, δ-, omega interferons, tau-interferons, consensus interferons, asialo-interferons.

The term "class II interferon" as used herein means an interferon selected from a group of interferons that all bind to receptor type II. Examples of class II interferons include γ-interferons.

Specific preferred examples of some of these agents are listed below:

antiviral agents: ribavirin and amantadine;
immunomodulatory agents: class I interferons, class II interferons and pegylated interferons;
HCV NS3 protease inhibitors;
other inhibitors of the HCV polymerase: nucleosidic and non-nucleosidic inhibitors;
inhibitor of another target in the HCV life cycle that inhibits a target selected from: NS3 helicase, HCV NS2/3 protease or internal ribosome entry site (IRES);
HIV inhibitors: nucleosidic inhibitors, non-nucleosidic inhibitors, protease inhibitors, fusion inhibitors and integrase inhibitors; or
HBV inhibitors: agents that inhibit viral DNA polymerase or is an HBV vaccine.

As discussed above, combination therapy is contemplated wherein a compound of formula (I), or a pharmaceutically acceptable salt thereof, is co-administered with at least one additional agent selected from: an antiviral agent, an immunomodulatory agent, an inhibitor of HCV NS3 protease, another inhibitor of HCV polymerase, an inhibitor of another target in the HCV life cycle, an HIV inhibitor, an HAV inhibitor and an HBV inhibitor. Examples of such agents are provided in the Definitions section above. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of wherein a compound of formula (I), or a pharmaceutically acceptable salt thereof.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood.

The following signs ---- and ⌇⌇⌇ are used interchangeably in subformulas to indicate the bond, or in the case of a spirocyclic group the atom, which is bonded to the rest of the molecule as defined.

As used herein, the designation whereby a bond to a substituent R is drawn as emanating from the center of a ring, such as, for example,

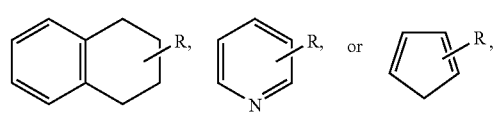

means that the substituent R may be attached to any free position on the ring that would otherwise be substituted by a hydrogen atom, unless specified otherwise.

PREFERRED EMBODIMENTS

As long as not stated otherwise, all groups, substituents and indices, like e.g. $R^1$, $R^2$, $R^{2h}$, $R^3$, $R^{4a}$, $R^{4b}$, $R^5$, $R^{11}$, $R^{12}$, $R^{13}$, $R^{21}$, $R^{31}$, $R^{32}$, $R^{33}$, $R^{35}$, $R^{60}$, $R^{111}$, $R^{112}$, $R^{117}$, $R^{150}$, $R^{160}$, $R^{161}$, $R^{162}$, $R^{163}$, $R^O$, $R^C$, $R^{N1}$, $R^{N2}$, $R^{N3}$, $R^{N4}$, A, B, $M^1$, $M^2$, $M^3$, $M^4$, $Y^1$, Z, HCy, and Het, have the definitions as defined hereinbefore and hereinafter. In the following, the preferred embodiments, groups, substituents and indices according to this invention are described.

In a preferred embodiment of the first aspect of the invention, there is provided an isomer, enantiomer, diastereoisomer or tautomer of a compound, represented by formula I:

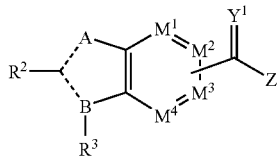
(I)

wherein
----- represents either a single or a double bond;
B is —N— and A is $CR^1$ or =N—; or
B is =C— and A is O, S or $NR^1$;
$R^1$ is selected from the group consisting of: H, $(C_{1-6})$alkyl optionally substituted with:
  halogen, $OR^{11}$, $SR^{11}$ or $N(R^{12})_2$, wherein $R^{11}$ and each $R^{12}$ is independently H, $(C_{1-6})$alkyl, $(C_{3-7})$cycloalkyl, $(C_{1-6})$alkyl-$(C_{3-7})$cycloalkyl, $(C_{1-6})$alkyl-aryl or $(C_{1-6})$alkyl-Het, said aryl or Het optionally substituted with $R^{160}$; or
  both $R^{12}$ are covalently bonded together and to the nitrogen to which they are both attached to form a 5, 6 or 7-membered saturated heterocycle;
the group —C(=$Y^1$)—Z is covalently linked to either $M^2$ or $M^3$,
$M^1$ is $CR^{4a}$,
one of $M^2$ and $M^3$ is $CR^5$,
$M^4$ is $CR^{4b}$,
and in addition one or two of the groups selected from $M^1$, $M^2$, $M^3$ and $M^4$ may also be N, with the proviso that the group $M^2$ or $M^3$ to which —C(=$Y^1$)—Z is linked is an C-atom,
$Y^1$ is O or S;
Z is defined as $NR^{N2}$—$SO_2$—$R^C$, wherein $R^C$ is optionally substituted with $R^{60}$;
$R^2$ is selected from: halogen or $R^{21}$, wherein $R^{21}$ is aryl or Het, said $R^{21}$ is optionally substituted with $R^{150}$;
$R^3$ is selected from $(C_{1-6})$alkyl, $(C_{3-7})$cycloalkyl, $(C_{1-3})$alkyl-$(C_{3-7})$cycloalkyl, $(C_{5-7})$cycloalkenyl, $(C_{1-3})$alkyl-$(C_{5-7})$cycloalkenyl, $(C_{6-10})$bicycloalkyl, $(C_{1-3})$alkyl-$(C_{6-10})$bicycloalkyl, $(C_{6-10})$bicycloalkenyl, $(C_{1-3})$alkyl-$(C_{6-10})$bicycloalkenyl, HCy or $(C_{1-3})$alkyl-HCy,
  wherein HCy is a saturated or unsaturated 4 to 7-membered heterocyclic group with 1 to 3 heteroatoms selected from O, S and N;
  said alkyl, cycloalkyl, cycloalkenyl, bicycloalkyl, bicycloalkenyl, HCy and alkyl-HCy being optionally substituted with from 1 to 4 substituents selected from:
    a) halogen;
    b) $(C_{1-6})$alkyl optionally substituted with:
      $OR^{31}$ or $SR^{31}$ wherein $R^{31}$ is H, $(C_{1-6}$alkyl), $(C_{3-7})$cycloalkyl or $(C_{1-3})$alkyl-$(C_{3-7})$cycloalkyl; or
      $N(R^{32})_2$ wherein each $R^{32}$ is independently H, $(C_{1-6})$alkyl, $(C_{3-7})$cycloalkyl or $(C_{1-3})$alkyl-$(C_{3-7})$cycloalkyl; or both $R^{32}$ are covalently bonded together and to the nitrogen to which they are attached to form a 5, 6 or 7-membered saturated heterocycle;
    c) $OR^{33}$ or $SR^{33}$ wherein $R^{33}$ is H, $(C_{1-6})$alkyl, $(C_{3-7})$cycloalkyl or $(C_{1-3})$alkyl-$(C_{3-7})$cycloalkyl;
    d) $N(R^{35})_2$ wherein each $R^{35}$ is independently H, $(C_{1-6})$alkyl, $(C_{3-7})$cycloalkyl or $(C_{1-3})$alkyl-$(C_{3-7})$cycloalkyl; or both $R^{35}$ are covalently bonded together and to the nitrogen to which they are attached to form a 5, 6 or 7-membered saturated heterocycle;
$R^{4a}$, $R^{4b}$, $R^5$ each are independently H or defined as $R^{150}$;
$R^{60}$ is defined as 1 to 4 substituents independently selected from:
  1 to 3 substituents selected from halogen;
  one of each substituent selected from: $OPO_3H$, $NO_2$, cyano, azido, C(=NH)$NH_2$, C(=NH)NH$(C_{1-6})$alkyl or C(=NH)NHCO$(C_{1-6})$alkyl, $SO_3H$; and
  1 to 3 substituents selected from:
    a) $(C_{1-6})$ alkyl, $(C_{3-7})$cycloalkyl, $C_{3-7}$ spirocycloalkyl optionally containing 1 or 2 heteroatom selected from N, O and S; $(C_{2-6})$alkenyl, $(C_{2-8})$alkynyl, $(C_{1-6})$alkyl-$(C_{3-7})$cycloalkyl, all of which optionally being substituted with $R^{150}$;
    b) $OR^O$;
    c) $OC(O)R^O$;
    d) $SR^O$, $SO_2R^C$, $SO_2N(R^{N2})R^{N1}$, $SO_2N(R^{N2})C(O)R^C$ or $CONR^{N2}SO_2R^C$;
    e) $N(R^{N2})R^{N1}N(R^{N2})COOR^C$ or $N(R^{N2})SO_2R^C$;
    f) $N(R^{N2})COR^C$;
    g) $N(R^{N3})CON(R^{N2})R^{N1}$;
    h) $N(R^{N3})COCOR^C$, $N(R^{N3})COCOOR^O$ or $N(R^{N3})CO$-$CON(R^{N2})R^{N1}$;
    i) $COR^O$;
    j) $COOR^O$;
    k) $CON(R^{N2})R^{N1}$;
    l) aryl, Het, $(C_{1-4}$alkyl)aryl or $(C_{1-4}$alkyl)Het, all of which optionally being substituted with $R^{150}$;
  wherein said $R^{N1}$, $R^C$ and/or $R^O$ are optionally substituted with $R^{150}$ as defined,
$R^{150}$ is defined as 1 to 4 substituents independently selected from:
  1 to 3 substituents selected from halogen;
  one of each substituent selected from: $OPO_3H$, $NO_2$, cyano, azido, C(=NH)$NH_2$, C(=NH)NH$(C_{1-6})$alkyl or C(=NH)NHCO$(C_{1-6})$alkyl; and
  1 to 3 substituents selected from:
    a) $(C_{1-6})$ alkyl, $(C_{3-7})$cycloalkyl, $C_{3-7}$ spirocycloalkyl optionally containing 1 or 2 heteroatoms selected from N, O and S; $(C_{2-6})$alkenyl, $(C_{2-8})$alkynyl, $(C_{1-3})$ alkyl-$(C_{3-7})$cycloalkyl, all of which optionally substituted with $R^{160}$;
    b) $OR^O$;
    c) $OC(O)R^O$;
    d) $SR^O$, $SO_2R^C$, $SO_2N(R^{N2})R^{N1}$ or $SO_2N(R^{N2})C(O)R^C$;
    e) $N(R^{N2})R^{N1}N(R^{N2})COOR^C$ or $N(R^{N2})SO_2R^C$;
    f) $N(R^{N2})COR^C$;
    g) $N(R^{N3})CON(R^{N2})R^{N1}$;
    h) $N(R^{N3})COCOR^C$, $N(R^{N3})COCOOR^O$ or $N(R^{N3})CO$-$CON(R^{N2})R^{N1}$;
      wherein $R^{N1}$ is as defined or OH, OAlkyl;
    i) $COR^O$;
    j) $COOR^O$;
    k) tetrazole or $CON(R^{N2})R^{N1}$;
  wherein said $R^{N1}$, $R^C$ and/or $R^O$ are optionally substituted with $R^{160}$ as defined;
$R^{160}$ is defined as 1, 2 or 3 substituents independently selected from:
  1, 2 or 3 fluorine substituents; and
  one of each substituent selected from tetrazole, chlorine, bromine, iodine, CN, nitro, $C_{1-4}$alkyl, $CF_3$, $COOR^{161}$, $SO_3H$, $SR^{161}$, $SO_2R^{163}$, $OR^{161}$, $N(R^{162})_2$, $SO_2N(R^{162})_2$, $SO_2NR^{162}COR^{162}$, $NR^{162}SO_2R^{163}$, $NR^{162}COR^{162}$ or CON($R^{162}$)$_2$, wherein $R^{161}$, $R^{163}$ and each $R^{162}$ is independently ($C_{1-4}$)alkyl, ($C_{3-7}$)cycloalkyl or ($C_{1-3}$)alkyl-($C_{3-7}$)cycloalkyl; and $R^{161}$ and each $R^{162}$ may each independently also be H; or both $R^{162}$ are covalently bonded together and to the nitrogen to which they are attached to form a 5, 6 or 7-membered saturated heterocycle;

$R^O$, $R^C$ are independently defined as ($C_{1-6}$)alkyl, ($C_{3-6}$)cycloalkyl, ($C_{1-4}$)alkyl-($C_{3-6}$)cycloalkyl, ($C_{2-6}$)alkenyl, aryl, Het, ($C_{1-4}$)alkyl-aryl, ($C_{1-4}$)alkyl-Het;

$R^{N1}$ is H, ($C_{1-6}$)alkyl, ($C_{3-7}$)cycloalkyl, ($C_{1-4}$)alkyl-($C_{3-6}$)cycloalkyl, ($C_{2-6}$)alkenyl, aryl, Het, ($C_{1-4}$)alkyl-aryl, ($C_{1-4}$)alkyl-Het; or $R^{N2}$, $R^{N3}$, $R^{N4}$ are independently H, $CH_3$, ($C_{2-6}$alkyl), ($C_{3-6}$)cycloalkyl, ($C_{1-4}$)alkyl-($C_{3-6}$)cycloalkyl; all of which being optionally substituted with halogen, carboxy or $C_{1-6}$-alkoxycarbonyl; and/or wherein said alkyl, cycloalkyl or alkylcycloalkyl is optionally substituted with hydroxy, $C_{1-6}$-alkyl, $C_{1-6}$-alkoxy, amino, —NH($C_{1-4}$-alkyl) and/or —N($C_{1-4}$-alkyl)$_2$; and in the case a) of a group N($R^{N2}$)$R^{N1}$ the substituents $R^{N2}$ and $R^{N1}$; or b) of a group NR$^{N3}$—N($R^{N2}$)$R^{N1}$ the substituents $R^{N3}$ and $R^{N1}$, or $R^{N2}$ and $R^{N1}$; may be covalently bonded together to form a 4-, 5-, 6- or 7-membered saturated or unsaturated N-containing heterocycle or a 8-, 9-, 10- or 11-membered N-containing heterobicycle each may have additionally from 1 to 3 heteroatoms selected from O, N, and S, wherein said heterocycle or heterobicycle is optionally substituted as defined;

wherein Het is defined as a 4-, 5-, 6- or 7-membered heterocycle having 1 to 4 heteroatoms selected from O, N and S, or a 8-, 9-, 10- or 11-membered heterobicycle having 1 to 5 heteroatoms selected from O, N and S;

or a salt thereof.

Core:

This invention comprises compounds of the formulas Ia and Ib (Ia)

(Ib)

Furthermore this invention comprises compounds according to the formulas I.1 to I.5

I.1

I.2

I.3

I.4

I.5

Preferably the groups $M^1$ and $M^4$ are $CR^{4a}$ and $CR^{4b}$, respectively. One group of $M^2$ and $M^3$ to which the group —C(=$Y^1$)—Z is covalently linked is preferably C and the other group of $M^3$ and $M^2$ is preferably $CR^5$.

Therefore those compounds are preferred which are described by the following formulas

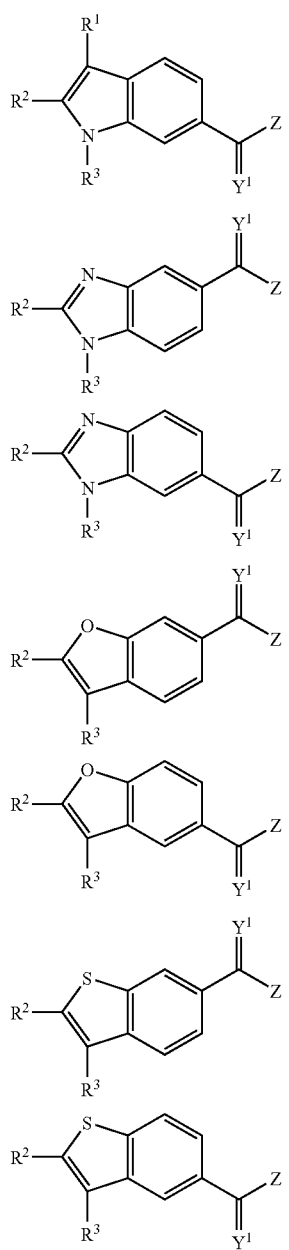

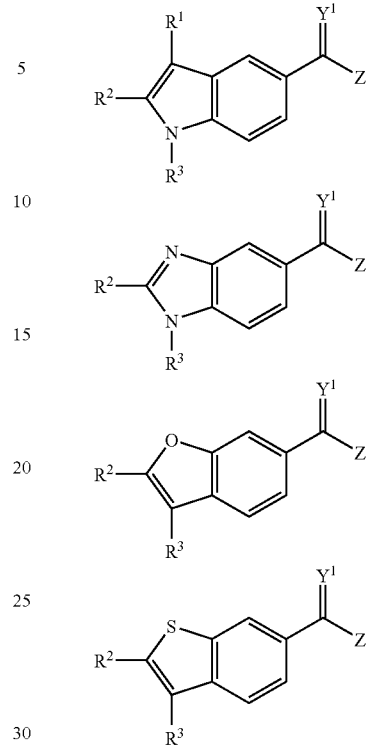

whereby the fused phenyl ring may be mono-, di- or tri-substituted, preferably mono- or di-substituted, with $R^{150}$.

Furthermore compounds defined by the following formulas also belong to this invention

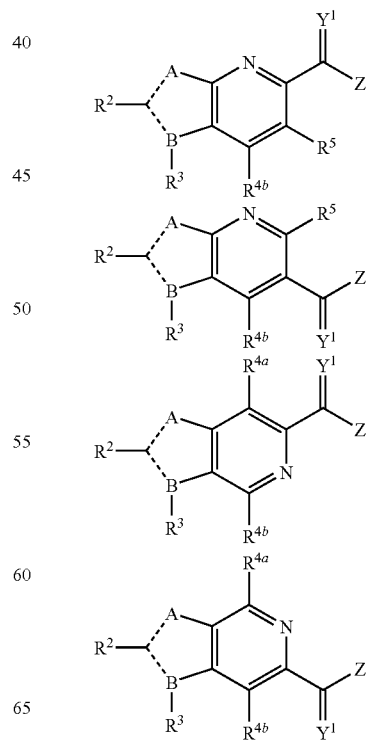

whereby the fused phenyl-ring may be mono-, di- or tri-substituted, preferably mono- or di-substituted, with $R^{150}$.

The most preferred compounds of the beforementioned formulas are described by the following formulas:

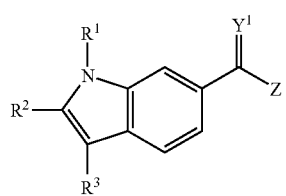

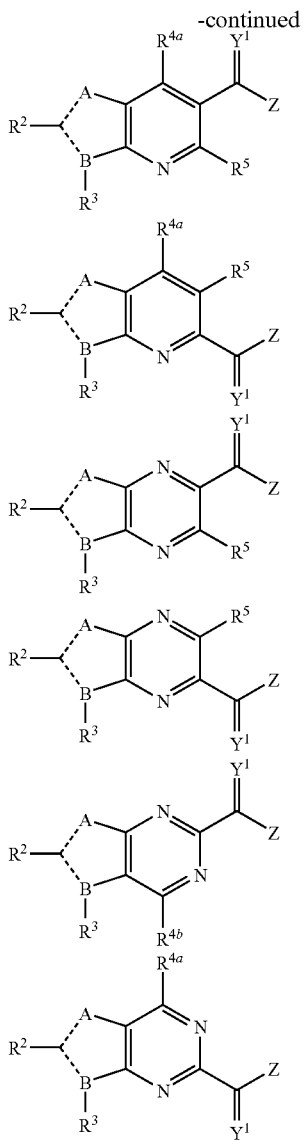

Yet furthermore, compounds defined by the following formulas also belong to this invention:

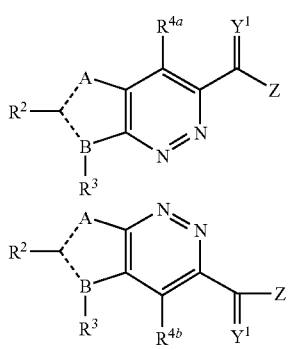

R¹:

According to a preferred embodiment of this invention R¹ is selected from the group consisting of H and $(C_{1-6})$alkyl, especially of H, $CH_3$, ethyl and isobutyl. Most preferably R¹ is H or methyl, in particular methyl.

$Y^1$:

A preferred definition of $Y^1$ is O.

Z:

According to a preferred embodiment Z is defined as $NR^{N3}$—$SO_2$—$N(R^{N2})R^{N1}$, wherein $R^{N1}$, $R^{N2}$ and $R^{N3}$ are defined as hereinbefore and $R^{N1}$ or any heterocycle formed by $R^{N1}$ and $R^{N2}$ is optionally substituted with $R^{60}$.

According to a second preferred embodiment Z is defined as $NR^{N2}$—$SO_2$—$R^C$, wherein $R^C$ and $R^{N2}$ are defined as hereinbefore and $R^C$ is optionally substituted with $R^{60}$. Most preferably, Z is defined as $NR^{N2}$—$SO_2$—$R^C$ wherein $R^{N2}$ and $R^C$ are defined as follows:

$R^{N2}$ is H, $(C_{1-4})$alkyl, $(C_{3-6})$cycloalkyl or $(C_{1-3})$alkyl-$(C_{3-6})$cycloalkyl; in particular H or methyl; most preferably H; and $R^C$ is $(C_{1-6})$alkyl, $(C_{3-6})$cycloalkyl, $(C_{1-3})$alkyl-$(C_{3-6})$cycloalkyl, $(C_{2-6})$alkenyl, phenyl, naphthyl, Het, $(C_{1-3})$alkyl-phenyl, $(C_{1-3})$alkyl-naphthyl, $(C_{1-3})$alkyl-Het, wherein said alkyl, cycloalkyl, alkyl-cycloalkyl, alkenyl, phenyl, naphthyl, Het, alkyl-phenyl, alkyl-naphthyl, or alkyl-Het, are all optionally substituted with 1 to 4 substituents selected from $R^{60}$; preferably selected from $R^{150}$.

In this embodiment the preferred definition of $R^C$ is methyl, ethyl, n-propyl, i-propyl, cyclopropyl, cyclobutyl, cyclopentyl, cyclopropylmethyl, cyclobutylmethyl, cyclopentylmethyl, pyrrolidine, piperidine, morpholine, thiomorpholine, piperazine, phenyl, naphthyl, benzyl, thiophene, furan, pyrrole, imidazole, pyrazole, oxazole, isoxazole, thiazole, pyridazine, pyrimidine, pyrazine, diazepine, azepine, quinoline, isoquinoline, benzofuran, benzothiophene, benzothiazole, purine, pteridine, 2,1,3-benzothiadiazole

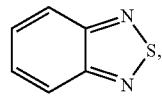

and imidazo[2,1-B][1,3]thiazole

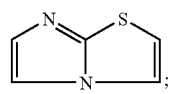;

all of which are optionally substituted with 1 to 3 substituents selected from $R^{60}$; preferably selected from $R^{150}$. Most preferred substituents thereof are halogen, nitro, $(C_{1-3})$alkyl, $O(C_{1-3})$alkyl, carboxyl, $COO(C_{1-3})$alkyl, $NHCO(C_{1-3})$alkyl, wherein the alkyl groups may be substituted by halogen.

$R^2$:

Preferably $R^2$ is $R^{21}$, wherein $R^{21}$ is a phenyl or Het selected from the group of formulas

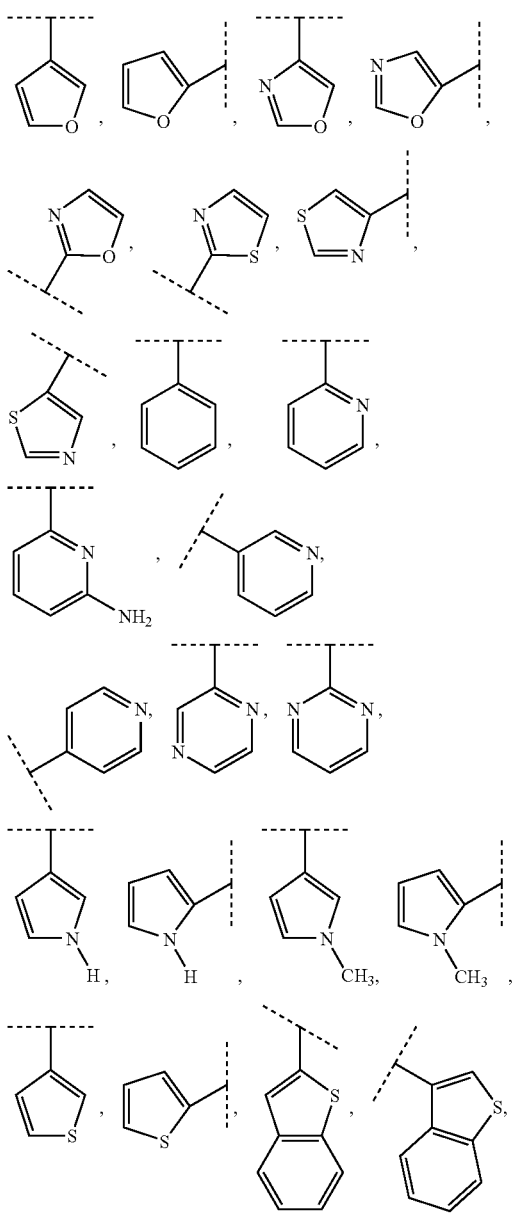

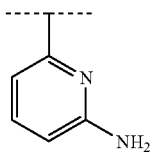

all of which may be unsubstituted or substituted as defined.

In the case $R^2$ as defined above is substituted, it is preferably substituted with 1, 2 or 3 substituents selected from:
1 to 3 substituents selected from halogen;
one of each substituent selected from: $NO_2$, cyano, azido; and
1 to 2 substituents selected from:
a) $(C_{1-4})$alkyl or $(C_{1-4})$alkoxy, both optionally substituted with OH, $O(C_{1-4})$alkyl, $SO_2(C_{1-4})$alkyl, 1 to 3 halogen atoms, amino, $NH(CH_3)$ or $N(CH_3)_2$);
b) $NR^{111}R^{112}$ wherein both $R^{111}$ and $R^{112}$ are independently $H(C_{1-4})$alkyl, or $R^{112}$ is $(C_{3-7})$cycloalkyl, $(C_{1-3})$alkyl$(C_{3-7})$ cycloalkyl, phenyl, benzyl; or both $R^{111}$ and $R^{112}$ are covalently bonded together and to the nitrogen to which they are attached to form a nitrogen-containing heterocycle, each of said alkyl, cycloalkyl, alkylcycloalkyl, phenyl and benzyl, being optionally substituted with halogen or: $—OR^{2h}$ or $N(R^{2h})_2$, wherein each $R^{2h}$ is independently H, $(C_{1-4})$alkyl, or both $R^{2h}$ are covalently bonded together and to the nitrogen to which they are attached to form a nitrogen-containing heterocycle;
c) $NHCOR^{117}$ wherein $R^{117}$ is $(C_{1-4})$alkyl, $O(C_{1-4})$alkyl or $O(C_{3-7})$cycloalkyl; and
e) $CONH_2$, $CONH(C_{1-4})$alkyl), $CON((C_{1-4})$alkyl$)_2$.

Most preferred substituents of $R^2$ are selected from:
1 to 2 substituents selected from fluorine;
one of each substituent selected from: chlorine, bromine, $NO_2$, cyano; and
1 to 2 substituents selected from:
a) methyl, trifluoromethyl, ethyl, n-propyl, i-propyl, methoxy, trifluoromethoxy, ethoxy, n-propoxy or i-propoxy, wherein said methyl, ethyl, n-propyl, i-propyl, ethoxy, n-propoxy and i-propoxy are optionally substituted with OH, methoxy, amino, $NH(CH_3)$ or $N(CH_3)_2$;
b) $NR^{111}R^{112}$ wherein both $R^{111}$ and $R^{112}$ are independently H or methyl, or $R^{112}$ is phenyl or benzyl;
c) $NHCOR^{117}$ wherein $R^{117}$ is methyl or methoxy; and
e) $CONH_2$, $CONH(CH_3)$, $CON(CH_3)_2$.

$R^3$:

$R^3$ is preferably selected from $(C_{3-7})$cycloalkyl, $(C_{5-7})$cycloalkenyl, $(C_{6-10})$bicycloalkyl, $(C_{6-10})$bicycloalkenyl, or HCy, wherein said groups are unsubstituted or mono- or disubstituted by halogen, hydroxy, $(C_{1-4})$alkyl and/or $O—(C_{1-4})$alkyl, wherein the alkyl groups may be fluorinated.

Most preferably $R^3$ is cyclopropyl, cyclobutyl, cyclopentyl, cyclohexyl or cycloheptyl, or a group selected from:

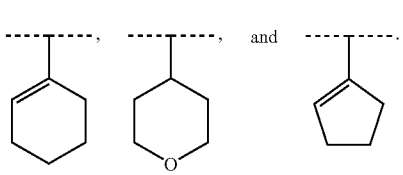

and wherein said $R^{21}$ is unsubstituted or substituted with $R^{150}$.

A very most preferred definition of $R^2$ is

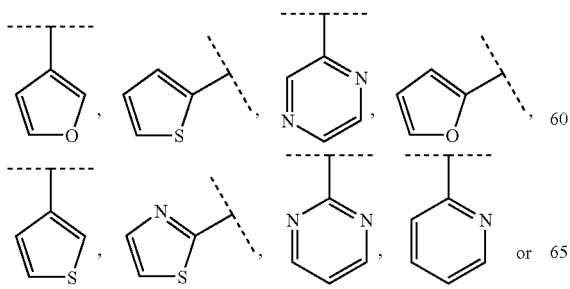

wherein all said cyclic groups are unsubstituted or substituted by fluorine, $(C_{1-3})$alkyl or $CF_3$.

The very most preferred definition of $R^3$ is cyclopentyl or cyclohexyl.

$R^{4a}$, $R^{4b}$, $R^5$:

Preferably $R^{4a}$, $R^{4b}$, $R^5$ each are independently H, hydroxy, halogen, cyano, nitro, carboxyl, $(C_{1-4})$alkyl, $CF_3$, $(C_{1-4})$alkoxy, —O—$(C_{3-7})$cycloalkyl, —O—$(C_{1-3})$alkyl-$(C_{3-7})$cycloalkyl, —O-aryl, —O—$(C_{1-3})$alkyl-aryl, —O-Het, —O—$(C_{1-3})$alkyl-Het, $NR^{N1}R^{N2}$, or $COR^O$, $NR^{N2}COR^C$, $CONR^{N2}R^{N1}$, $NR^{N3}CONR^{N1}R^{N2}$, in particular $NHCO(C_{1-4})$alkyl or $CONHR^{N1}$, $NHCONHR^{N1}$;

wherein $R^C$, $R^O$, $R^{N1}$, $R^{N2}$, $R^{N3}$ are as defined; preferably $R^C$, $R^O$ and $R^{N1}$ are independently of each other H, $(C_{1-4})$alkyl, aryl, $(C_{1-3})$alkyl-aryl, wherein aryl is preferably optionally substituted phenyl; and preferably $R^{N2}$ and $R^{N3}$ are independently H or methyl; wherein all said alkyl groups, including alkoxy, may be mono-, di- or trisubstituted by fluorine or mono-substituted by chlorine or bromine.

Most preferred substituents $R^{4a}$, $R^{4b}$, $R^5$ each are independently H, hydroxy, halogen, cyano, nitro, methyl, $CF_3$, methoxy, carboxy, amino, —$NMe_2$, —$CONH_2$, —$NHCONH_2$, —CO—$NHMe$, —$NHCONHMe$, —CO-$NMe_2$ or —NH-$CONMe_2$; in particular H, methyl or methoxy. Preferably $R^{4a}$ is H or methyl. Very most preferably at least two of the substituents selected from $R^{4a}$, $R^{4b}$, $R^5$ are H.

$R^{60}$:

The substituents $R^{60}$ are preferably each defined as 1 to 4 substituents independently selected from:

1 to 3 substituents selected from halogen;
one of each substituent selected from: $NO_2$, cyano, azido; and
1 to 3 substituents selected from:
a) $(C_{1-4})$ alkyl, $(C_{3-7})$cycloalkyl, $(C_{2-4})$alkenyl, $(C_{2-4})$alkynyl, $(C_{1-3})$alkyl-$(C_{3-7})$cycloalkyl, all of which optionally being substituted with $R^{150}$;
b) $OR^O$;
e) $N(R^{N2})R^{N1}$;
f) $N(R^{N2})COR^C$;
j) $COOR^O$;
k) $CON(R^{N2})R^{N1}$;
l) phenyl, Het, $(C_{1-3}$alkyl)phenyl or $(C_{1-3}$alkyl)Het; wherein Het is selected from furan, tetrahydrofuran, thiophene, tetrahydrothiophene, tetrahydropyran, pyridinyl, azetidine, pyrrolidine, piperidine, piperazine, morpholine, thiomorpholine, homopiperidine and homopiperazine;

wherein said $R^{N1}$, $R^C$ and/or $R^O$ are optionally substituted with $R^{150}$ as defined.

$R^{150}$:

$R^{150}$ is preferably defined as 1 to 4 substituents independently selected from:

1 to 3 fluorine-substituents;
one of each substituent selected from: chlorine, bromine, iodine, $NO_2$, cyano, azido; and
1 to 3 substituents selected from:
a) $(C_{1-3})$ alkyl, $CF_3$, $(C_{3-6})$cycloalkyl, $(C_{1-3})$ alkyl-$(C_{3-6})$cycloalkyl, all of which optionally substituted with $R^{160}$;
b) $OR^O$;
e) $N(R^{N2})R^{N1}$;
f) $N(R^{N2})COR^C$;
j) $COOR^O$;
k) $CON(R^{N2})R^{N1}$;

wherein said $R^{N1}$, $R^C$ and/or $R^O$ are optionally substituted with $R^{160}$ as defined.

$R^{160}$:

$R^{160}$ is preferably defined as 1, 2 or 3 substituents independently selected from:

1, 2 or 3 fluorine substituents; and
one of each substituent selected from chlorine, bromine, iodine, CN, nitro, methyl, trifluoromethyl, ethyl, n-propyl, i-propyl, COOH, $COOCH_3$, OH, $OCH_3$, $OCF_3$, $NH_2$, $NHCH_3$, $N(CH_3)_2$, $SO_2NH_2$, $NHCOCH_3$, $SO_2NHCOCH_3$ or $CONH_2$, $CONHCH_3$ and $CON(CH_3)_2$.

$R^O$, $R^C$:

Preferably $R^O$, $R^C$ are independently selected from $(C_{1-4})$ alkyl, $(C_{3-6})$cycloalkyl, $(C_{1-3})$alkyl-$(C_{3-6})$cycloalkyl, phenyl, benzyl, Het, $(C_{1-3})$alkyl-Het; all of which are optionally substituted as defined; and $R^O$ may also be H.

$R^{N1}$, $R^{N2}$, $R^{N3}$, $R^{N4}$:

$R^{N1}$ is preferably selected from H, $(C_{1-4})$alkyl, $(C_{3-6})$cycloalkyl, $(C_{1-3})$alkyl-$(C_{3-6})$cycloalkyl, phenyl, benzyl, phenylethyl, Het, $(C_{1-3})$alkyl-Het; wherein said alkyl, cycloalkyl, alkyl-cycloalkyl, phenyl, benzyl, phenylethyl, Het and alkyl-Het are optionally substituted as defined; or $R^{N2}$, $R^{N3}$, $R^{N4}$ are independently selected from H, methyl, ethyl, n-propyl, i-propyl, cyclopropyl, cyclopropylmethyl; all of which being optionally substituted with methyl, fluorine, carboxy or methoxycarbonyl; and/or wherein said ethyl, n-propyl or i-propyl, but preferably not the C-atom thereof directly bonded to the N-atom, is optionally substituted with hydroxy, methyl, methoxy, amino, —NH $(CH_3)$ and/or —$N(CH_3)_2$; and in the case
a) of a group $N(R^{N2})R^{N1}$ the substituents $R^{N2}$ and $R^{N1}$; or
b) of a group $NR^{N3}$—$N(R^{N2})R^{N1}$ the substituents $R^{N3}$ and $R^{N1}$ or $R^{N2}$ and $R^{N1}$;

may be covalently bonded together to form a 5-, 6- or 7-membered saturated heterocycle which may have additionally one heteroatom selected from O, N, and S, wherein said heterocycle is optionally substituted as defined.

Included within the scope of this invention are all compounds of formula I as presented in Tables 1 and 2. Preferred compounds of these tables show an $IC_{50}$ value of below 1 μM (range B as defined hereinafter).

Polymerase Activity

The ability of the compounds of formula (I) to inhibit RNA synthesis by the RNA dependent RNA polymerase of HCV can be demonstrated by any assay capable of measuring RNA dependent RNA polymerase activity. A suitable assay is described in the examples.

Specificity for RNA Dependent RNA Polymerase Activity

To demonstrate that the compounds of the invention act by specific inhibition of HCV polymerase, the compounds may be tested for inhibitory activity in an assay measuring the activity of an RNA-dependent RNA polymerase other than the HCV polymerase or in a DNA dependent RNA polymerase assay.

When a compound of formula (I), or one of its therapeutically acceptable salts, is employed as an antiviral agent, it is administered orally, topically or systemically to mammals, e.g. humans, cattle, pig, dogs, cats, rabbits or mice, in a vehicle comprising one or more pharmaceutically acceptable carriers, the proportion of which is determined by the solubility and chemical nature of the compound, chosen route of administration and standard biological practice.

For oral administration, the compound or a therapeutically acceptable salt thereof can be formulated in unit dosage forms such as capsules or tablets each containing a predetermined amount of the active ingredient, ranging from about 25 to 500 mg, in a pharmaceutically acceptable carrier.

For topical administration, the compound can be formulated in pharmaceutically accepted vehicles containing 0.1 to 5 percent, preferably 0.5 to 5 percent, of the active agent. Such formulations can be in the form of a solution, cream or lotion.

For parenteral administration, the compound of formula (I) is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in pharmaceutical texts, e.g. in "Remington's The Science and Practice of Pharmacy", 19th ed., Mack Publishing Company, Easton, Pa., 1995, or in "Pharmaceutical Dosage Forms And Drugs Delivery Systems", 6th ed., H. C. Ansel et al., Eds., Williams & Wilkins, Baltimore, Md., 1995.

The dosage of the compound will vary with the form of administration and the particular active agent chosen. Furthermore, it will vary with the particular host under treatment. Generally, treatment is initiated with small increments until the optimum effect under the circumstance is reached. In general, the compound of formula I is most desirably administered at a concentration level that will generally afford antivirally effective results without causing any harmful or deleterious side effects.

For oral administration, the compound or a therapeutically acceptable salt is administered in the range of 10 to 200 mg per kilogram of body weight per day, with a preferred range of 25 to 150 mg per kilogram.

For systemic administration, the compound of formula (I) is administered at a dosage of 10 mg to 150 mg per kilogram of body weight per day, although the aforementioned variations will occur. A dosage level that is in the range of from about 10 mg to 100 mg per kilogram of body weight per day is most desirably employed in order to achieve effective results.

When the compositions of this invention comprise a combination of a compound of formula I and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit HCV polymerase or to treat or prevent HCV virus infection. Such treatment may also be achieved using the compounds of this invention in combination with agents which include, but are not limited to: immunomodulatory agents, such as α-, β-, or γ-interferons; other antiviral agents such as ribavirin, amantadine; other inhibitors of HCV NS5B polymerase; inhibitors of other targets in the HCV life cycle, which include but are not limited to, helicase, NS2/3 protease, NS3 protease, or internal ribosome entry site (IRES); or combinations thereof.

The additional agents may be combined with the compounds of this invention to create a single dosage form. Alternatively these additional agents may be separately administered to a mammal as part of a multiple dosage form.

Methodology and Synthesis

The synthesis of compounds according to this invention is preferably accomplished by applying the procedures as outlined in the examples, including any adaptation of these procedures and/or applying additional synthesis steps known to the person skilled in the art. For example, carboxylic acid or thiocarboxylic acid intermediates (I" in the schemes described hereinafter) required in the preparation of compounds of formula I can be prepared by procedures, or adaptations thereof, described in WO 03/010141 or WO 02/04425.

EXAMPLES

The present invention is illustrated in further detail by the following non-limiting examples. All reactions are performed in a nitrogen or argon atmosphere. Temperatures are given in degrees Celsius. Flash chromatography is performed on silica gel. Solution percentages or ratios express a volume to volume relationship, unless stated otherwise. Mass spectral analyses are recorded using electrospray mass spectrometry. Hereinbefore and hereinafter the following abbreviations or symbols are used:

AcOH: acetic acid;

BOP: benzotriazole-1-yloxy-tris(dimethylamino)phosphonium hexafluorophosphate;

BroP: Bromo tris(dimethylamino)phosphonium hexafluorophosphate;

Bu: butyl;

DCC: 1,3-Dicyclohexyl carbodiimide;

DCM: dichloromethane;

DIEA: diisopropylethylamine;

DMAP: 4-(dimethylamino)pyridine;

DMF: N,N-dimethylformamide;

DMSO: dimethylsulfoxide;

EDAC: see EDC;

EDC: 1-(3-dimethylaminopropyl)-3-ethyl carbodiimide hydrochloride;

ES$^-$: electro spray (negative ionization);

ES$^+$: electro spray (positive ionization);

Et: ethyl;

Et$_2$O: diethyl ether;

EtOAc: ethyl acetate;

EtOH: ethanol;

HATU: O-(7-azabenzotriazol-1-yl)-N,N,N',N'-tetramethyluronium hexafluorophosphate;

HPLC: high performance liquid chromatography;

$^i$Pr: isopropyl;

$^i$PrOH: isopropanol;

Me: methyl;

MeCN: acetonitrile;

MeOH: methanol;

MS (ES): electrospray mass spectrometry;

Ph: phenyl;

Ra—Ni: Raney nickel

RT: room temperature (approximately 25° C.)

TBME: tert-butylmethyl ether;

TBTU: 2-(1H-benzotriazol-1-yl)-N,N,N',N'-tetramethyluronium tetrafluoroborate;

tBu: tert.-butyl;

TFA: trifluoroacetic acid;

THF: tetrahydrofuran;

TLC: thin layer chromatography;

Example 1

General Procedure for the Preparation of Acylsulfonamides of General Formula I

Acylsulfonamide derivatives of the general formula I ($Z=NR^{N2}SO_2R^C$) according to this invention are preferably prepared by firstly activating the carboxyl group (or thio analog) of the corresponding carboxylic acid derivative (or thio analog) of formula I' and secondly condensing the activated carboxylic acid derivative (or thio analog) with sulfonamides using standard procedures as depicted in the following scheme.

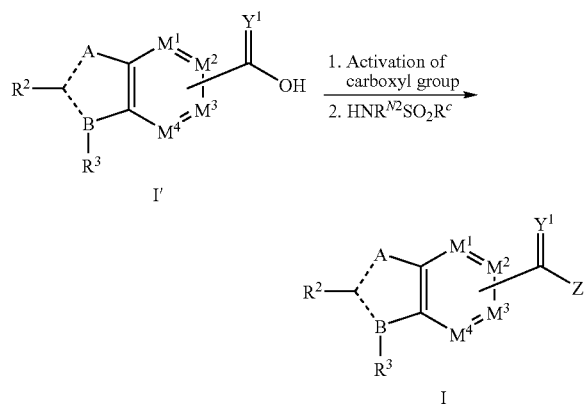

wherein A, B, $M^1$ to $M^4$, $R^2$, $R^3$, $Y^1$, Z, $R^{N2}$ and $R^C$ are as defined hereinbefore, Z is defined as $NR^{N2}SO_2R^C$ and --- represents either a single or double bond.

The carboxylic acid derivative (or thio analog) of formula I', including esters thereof, are preferably synthesized according or in analogy to the procedures as outlined in WO 03/010141 and WO 02/04425.

Activation of carboxylic acids such as those described in the scheme above, can be accomplished using standard amide bond forming reagents such as TBTU, HATU, BOP, BroP, EDAC, DCC, isobutyl chloroformate and the like. Alternatively, activation of the carboxyl group is accomplished by conversion to the corresponding acid chloride prior to condensation with a sulfonamide. Sulfonamides can be obtained from commercial sources or prepared from the corresponding sulfonyl chlorides using a solution of ammonia in an inert solvent such as dioxane, THF and the like.

Example 2

General Procedure for the Preparation of Acylsulfonyldiamides of General Formula I Acylsulfonyldiamide derivatives of general formula I ($Z=NR^{N3}SO_2N(R^{N2})R^{N1}$) are prepared by condensation of carboxylic acid derivative of general formula I' (or thio analog) with sulfonyldiamides using standard procedures as depicted in the scheme below.

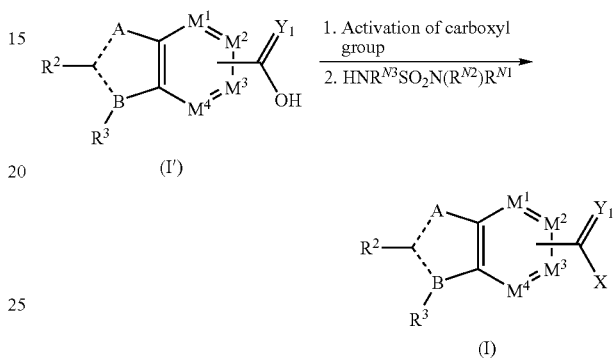

wherein A, B, $M^1$ to $M^4$, $R^2$, $R^3$, $Y^1$, $R^{N1}$, $R^{N2}$ and $R^{N3}$ are as defined hereinbefore, Z is defined as $NR^{N3}SO_2N(R^{N2})R^{N1}$ and --- represents either a single or double bond.

The carboxylic acid derivative (or thio analog) of formula I', including esters thereof, are preferably synthesized according or in analogy to the procedures as outlined in WO 03/010141 and WO 02/04425.

Activation of carboxylic acids such as those described in the scheme, can be accomplished using standard amide bond forming reagents such as TBTU, HATU, BOP, BroP, EDAC, DCC, isobutyl chloroformate and the like. Alternatively, activation of the carboxyl group is accomplished by conversion to the corresponding acid chloride prior to condensation with a sulfonyldiamide. Sulfonyldiamides of formula $HNR^{N3}SO_2N(R^{N2})R^{N1}$, as required in the second step of the scheme, can be prepared by known methods, such as heating amines of formula $R^{N3}NH_2$ with sulfamide in an appropriate solvent (e.g. dioxane) at temperatures ranging from 80 to 160° C. Such procedures are exemplified in the literature (e.g. R. Sarges *Journal of Medicinal Chemistry* 1976, 19, 695-709).

Example 3

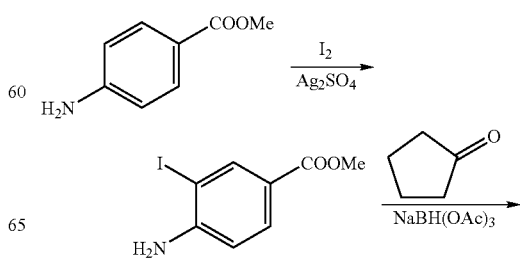

-continued

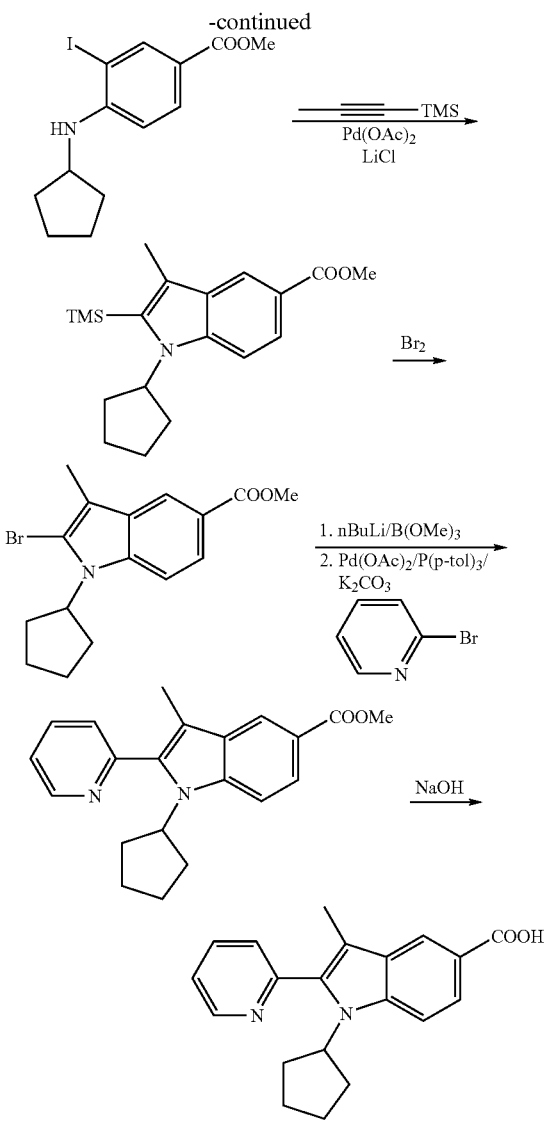

Methyl 4-amino-3-iodobenzoate

Methyl 4-aminobenzoate (30.23 g, 200 mmol) was added to a mixture of iodine (60.91 g, 240 mmol) and silver sulfate (81.07 g, 260 mmol) in 1 L of ethanol at room temperature. The mixture was stirred at room temperature for 18 hours, filtered over Celite and the filtrate was evaporated to dryness under reduced pressure. The residue was chromatographed on silica gel (230-400 mesh) and eluted with 1% ethyl acetate in hexane to give 35 g (63%).

Methyl 4-(N-cyclopentylamino)-3-iodobenzoate

A mixture of methyl 4-amino-3-iodobenzoate from above (27.69 g, 100 mmol), cyclopentanone (52.8 mL, 600 mmol), and anhydrous sodium sulfate (1000 g, 142 mmol) in 500 mL of glacial acetic acid was stirred for two hours. Solid sodium triacetoxyborohydride (76.92, 345 mmol) was added in portions and stirred for 16 hrs at room temperature. The mixture was poured on to cool 900 mL of saturated aqueous sodium bicarbonate solution carefully and extracted with 150 mL (3×) of ethyl acetate. The ethyl acetate fraction was dried and evaporated. Purification with silica gel and 0.5% ethyl acetate in hexane gave 24 g (70%).

Methyl 1-cyclopentyl-3-methyl-2-trimethylsilylindole-5-carboxylate

A mixture of methyl 4-(N-cyclopentylamino)-3-iodobenzoate from above (22.42 g, 65 mmol), palladium acetate (738 mg, 3.28 mmol), lithium chloride (2.757 g, 65 mmol), potassium acetate (12.757 g, 92.30 mmol), and 1-trimethylsilyl-1-propyne (28.70 mL, 192.56 mmol) in 390 mL of DMF was heated at 100° C. for 6 hours. The mixture was added onto 500 mL of saturated aqueous ammonium chloride solution and extracted with ethyl acetate. The ethyl acetate fraction was dried, evaporated and semi-purified by flash chromatography using silica gel and 0.1% ethyl acetate in hexane. Adding hexane to the semi-purified compound gave 16 g of white crystals (75%).

Methyl 2-bromo-1-cyclopentyl-3-methylindole-5-carboxylate

1-Cyclopentyl-3-methyl-2-trimethylsilylindole-5-carboxylate from above (16.45 g, 50 mmol) was dissolved in 500 mL of dichloromethane, cooled to 0° C. A solution of bromine (1 M, 45 mL, 45 mmol) in dichloromethane was added slowly and stirred for 30 minutes. The solvent was evaporated under reduced pressure, chromatographed on silica gel with 0.1% ethyl acetate to give a semi-pure compound. Addition of hexane gave 12 g (71%).

Methyl 1-cyclopentyl-3-methyl-2-(2-pyridyl)indole-5-carboxylate

The 2-bromoindole from above (1.53 g, 4.55 mmol, 1.0 equiv.) was dissolved in anhydrous THF (20 mL) and the solution was cooled to −78° C. under an argon atmosphere. N-BuLi (solution in hexane, 4.78 mmol, 1.05 equiv.) was added dropwise and the mixture was stirred 30 min in the cold. Trimethylborate (0.62 mL, 5.46 mmol, 1.2 equiv.) was added dropwise and the solution stirred at −78° C. for 40 min and then at 0° C. for 1 h. Finally the reaction mixture was allowed to warm up to room temperature and additional THF (20 mL) was added. para-Tolylphosphine (0.083 g, 0.27 mmol, 0.06 equiv.) and 2-bromopyridine (0.86 g, 5.46 mmol, 1.2 equiv.) were then added and the solution was degassed by bubbling argon through for 30 min. Palladium acetate (10 mg, 0.046 mmol, 0.01 equiv.), anhydrous potassium carbonate (1.26 g, 9.1 mmol, 2 equiv.) and MeOH (20 mL) were added and the mixture was refluxed overnight under an argon atmosphere. After cooling to RT, TBME (12 mL) and water (12 mL) were added, the organic phase was separated and the aqueous phase extracted with additional TBME (2×25 mL). The combined organic layers were washed with brine, dried (Na$_2$SO$_4$) and concentrated to give a residue that was purified by flash chromatography on silica gel using 5-10% EtOAc in hexane as eluent: 1.21 g (79%).

1-Cyclopentyl-3-methyl-2-(2-pyridyl)indole-5-carboxylic acid

The methyl ester from above (1.10 g, 3.29 mmol) was dissolved in 1:1 THF-MeOH (10 mL) and 6 N aqueous NaOH (4.2 mL, 5 equiv.) was added. The mixture was stirred for 3 h at 60° C. The reaction mixture was cooled to RT and water (15 mL) was added. The suspension was filtered and the yellow filtrate washed with TBME (2×20 mL) and hexane (20 mL). Conc. HCl (1.9 mL) was added dropwise with stirring to pH 8, followed by AcOH (3 mL) to pH 2. The suspension was cooled and the white solid collected by filtration. The product was then dried under vacuum: 0.90 g (86%).

Example 4

3-Cyclohexyl-2-furan-3-yl-7-methyl-1H-indole-6-carboxylic acid methyl ester

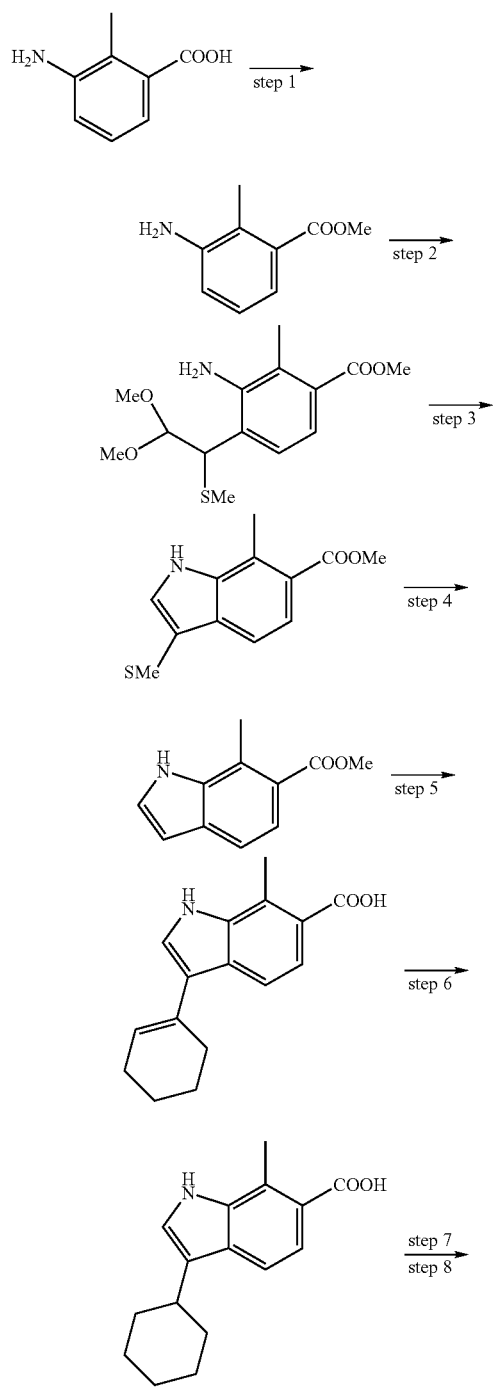

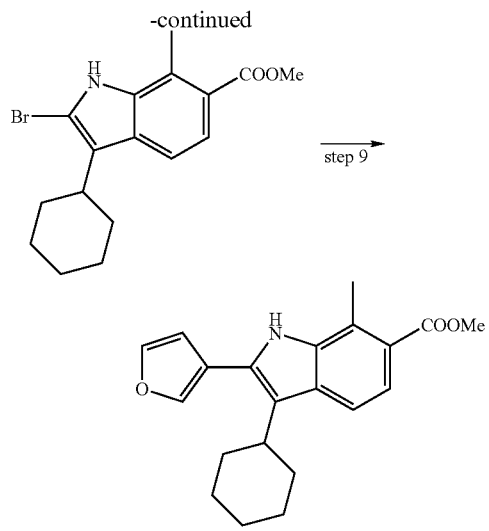

Step 1: 3-Amino-2-methylbenzoic acid (15.00 g, 0.099 mol) was suspended in MeOH (150 mL) and thionyl chloride (25.33 mL, 0.347 mole, 3.5 equiv.) was added dropwise. The mixture was heated overnight at 70° C. After cooling to RT, volatiles were removed under reduced pressure and the residue triturated with ether (150 mL). The solid was filtered off and dried (18.36 g). The solid was suspended in DCM (600 mL) and saturated aqueous NaHCO$_3$ (250 mL) was added. After stirring for 15 minutes, the organic layer was separated and washed successively with NaHCO$_3$ solution (2×250 mL), water (250 mL) and brine (250 mL). The solution was dried (Na$_2$SO$_4$), filtered and evaporated to dryness to give the desired aniline (14.8 g, 90% yield).

Steps 2 and 3: The ester obtained in the previous step (12.50 g, 75.6 mmol) was dissolved in DCM (190 mL) and methylthioacetaldehyde dimethyl acetal (10.1 mL, 75.6 mmol) was added. The solution was cooled to −30° C. N-chlorosuccinimide (10.10 g, 75.6 mmol) was added in 6 portions over 30 minutes. Triethylamine (10.6 mL, 75.6 mmol) was then added dropwise over 10 min and after stirring for an additional 15 min, the cooling bath was removed and the temperature brought to reflux. After 5 h, the reaction mixture was cooled to RT and evaporated to dryness. The residue was dissolved in ether (750 mL) and 2M HCl (303 mL) was added. After stirring at RT for 1.5 h, the ether layer was separated and washed with NaHCO$_3$ solution (2×150 mL) and brine (250 mL). The original acidic aqueous phase was extracted with DCM (2×100 mL) and the extracts washed as above and then combined with the first ether phase. The combined organic phases were dried (Na$_2$SO$_4$) and evaporated to dryness and the material purified by flash chromatography on silica gel using 30-0% hexane in DCM as eluent to give the desired 3-thiomethylindole derivative (9.37 g).

Step 4: The thiomethyl indole obtained in the previous step (8.37 g, 35.4 mmol) was dissolved in absolute EtOH (220 mL) and Raney-nickel (Ra—Ni, 25 g) was added. After stirring at RT for 3 h, another portion of Ra—Ni (15 g) was added and stirring resumed for an additional 45 min. The mixture was filtered and the filtrate evaporated to dryness to give the desired indole (6.26 g, 93%).

Step 5: The indole ester obtained in the previous step (4.00 g, 21 mmol) was dissolved in a mixture of MeOH (18 mL) and water (18 mL). KOH (11.86 g, 210 mmol) was added and the mixture stirred at 75° C. for 2 h. Cyclohexanone (7.26 g, 74 mmol, 3 equiv.) was added dropwise over 15 min and stirring at 75° C. was continued overnight. MeOH was removed under reduced pressure and water (500 mL) was added to the residue. Insoluble material was removed by filtration and the aqueous phase was then washed with TBME (200 mL). The aqueous phase was acidified to pH 4 with formic acid to produce a white precipitate that was collected by filtration, washed with water and dried. The desired cyclohexenylindole was obtained (4.77 g, 89%).

Step 6: The cyclohexene derivative from above (4.70 g, 18 mmol) was dissolved in MeOH (1 L) and 20% Pd(OH)$_2$ on C (0.24 g) was added. The mixture was hydrogenated (60 psi of H$_2$ gas) for 7 h, filtered, and then concentrated under reduced pressure. The residue was triturated with MeOH (100 mL), and the solid collected by filtration and dried (3.50 g)

Step 7: The carboxylic acid from step 6 (3.44 g, 13 mmol) was dissolved in DMF (22 mL) and anhydrous K$_2$CO$_3$ (2.55 g, 18 mmol) was added followed by iodomethane (2.09 g, 15 mmol). The mixture was stirred overnight at room temperature and then poured into water (60 mL) and acidified to pH 4 with 4 N HCl (10 mL). The product was extracted with ether (3×150 mL) and washed with water (4×90 mL) and brine (90 mL). After drying (Na$_2$SO$_4$) and removal of solvents, the desired methyl ester was obtained as a white solid (3.44 g).

Step 8: The indole derivative of step 7 (3.20 g, 12 mmol) was dissolved in a mixture of THF (30 mL) and CHCl$_3$ (30 mL) and the solution cooled to −5° C. Pyridinium tribromide (5.17 g, 16 mmol) was added in portions maintaining the internal temperature at −5° C. After stirring for 1 h at −5° C., the reaction was allowed to warm up to room temperature and concentrated to dryness. Water (50 mL) was added and the product extracted with ether (3×100 mL). The extract was washed with water (2×90 mL) and brine (90 mL) and dried (Na$_2$SO$_4$). Removal of solvents under reduced pressure gave a residue that was purified by flash chromatography using 10% EtOAc in hexane as eluent. The desired bromide was obtained as a solid (3.23 g).

Step 9: The bromoindole of step 8 (3.10 g, 8.9 mmol) was dissolved in a mixture of toluene (20 mL), EtOH (20 mL) and water (14 mL). 3-Furylboronic acid (1.27 g, 11.3 mmol), LiCl (0.75 g, 17.7 mmol) and Na$_2$CO$_3$ (2.35 g, 22.1 mmol) were added. The solution was degassed by bubbling argon gas for 30 min and tetrakis(triphenylphosphine)palladium° (0.41 g, 0.35 mmol) was added. The mixture was heated to 80° C. for 3 h, cooled to room temperature and extracted with TBME (350 mL) using water (90 mL) for rinsing undissolved solids. The organic phase was separated and the aqueous phase extracted twice more with TBME (2×150 mL). The combined extracts were washed with water (2×100 mL) and brine (100 mL), dried (Na$_2$SO$_4$) and concentrated to dryness. The residue was purified by flash chromatography using 5-15% EtOAc in hexane as eluent (3.0 g). The protected indole from above can be saponified to the free carboxylic acid as described in example 3.

Example 5

Methyl 2-bromo-3-cyclohexyl-1H-indole-5-carboxylate and 3-cyclohexyl-2-furan-3-yl-1H-indole-5-carboxylic acid

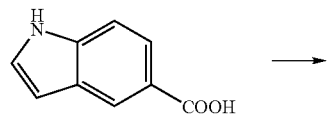

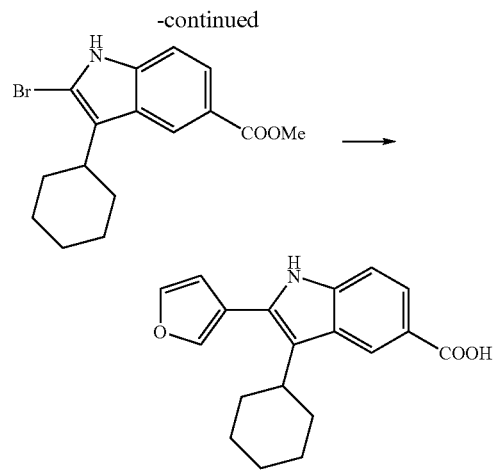

Using the same series of reactions described in example 2 of WO 03/010141 but starting from indole 5-carboxylic acid, methyl 2-bromo-3-cyclohexyl-1H-indole-5-carboxylate was obtained and elaborated to 3-cyclohexyl-2-furan-3-yl-1H-indole-5-carboxylic acid using protocols such as those described in examples 3 and 4.

Example 6

7-Methoxy-1H-indole-6-carboxylic acid methyl ester

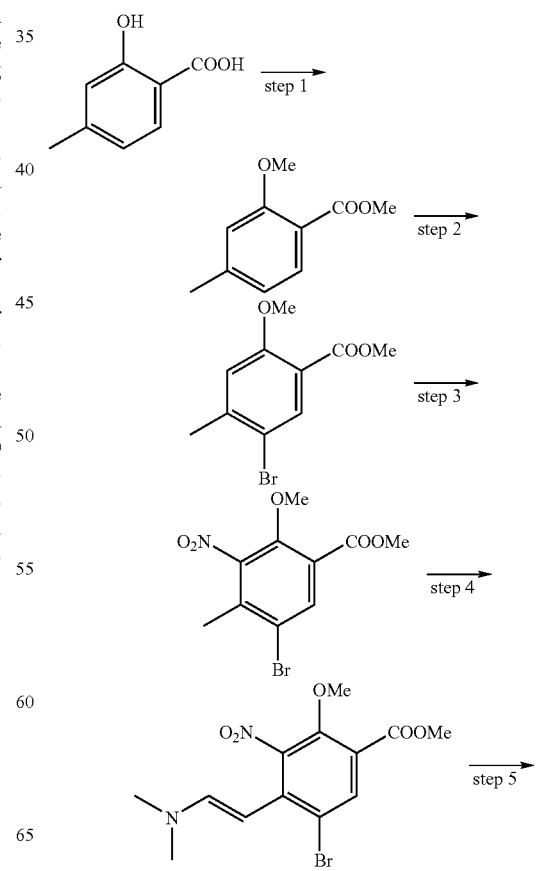

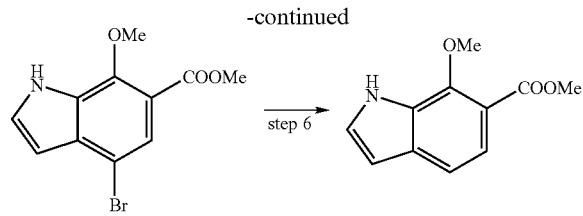

Step 1: 4-Methylsalicylic acid (32.1 g, 0.21 mol) and potassium carbonate (61.2 g, 0.44 mol) were suspended in acetone (300 mL) and the mixture brought to reflux temperature. Dimethyl sulfate (66.5 g, 0.53 mol) was added dropwise within 1 h and stirring continued overnight at reflux. Additional dimethylsulfate (30 mL) and potassium carbonate (2×15 g) were added and refluxing for an additional 24 h was required to complete the reaction. The reaction mixture was then cooled to room temperature and inorganic salts removed by filtration using acetone for washings. The filtrate was evaporated under reduced pressure and the oily residue was dissolved in MeOH (300 mL). Concentrated ammonium hydroxide (90 mL) was added and the mixture was stirred for 30 minutes at room temperature. Methanol was removed in vacuo and the residue portioned between ether (300 mL) and water (200 mL). The organic phase was separated and washed with brine and dried ($Na_2SO_4$). Evaporation of the ether gave the desired di-methylated product as a yellow oil (38.1 g) that was used directly in the next step.

Step 2: The ester obtained in the previous step (38.0 g, 0.21 mol) was dissolved in AcOH (250 mL) and bromine (37.2 g, 0.23 mole, 1.1 equiv.) was added dropwise over 30 min with stirring at room temperature. After completion, the reaction mixture was stirred for an additional hour, at which point TLC analysis indicated complete conversion. The reaction mixture was poured into water (1 L) and solid $Na_2CO_3$ was added cautiously with stirring until the mixture was neutral. The off-white precipitate that formed was collected by filtration, washed with water and dried to give the desired bromo derivative (47.2 g).

Step 3: The bromo derivative obtained in the previous step (44.5 g, 0.17 mol) was added in small portions to conc. $H_2SO_4$ (170 mL) and the mixture was stirred in an ice-salt bath until all solids dissolved. Conc. $HNO_3$ (17 mL) was then added dropwise over 20 min and stirring continued for an additional hour in the ice bath. The reaction mixture was then slowly added to ice-water (2 L) and the precipitated yellow solid was collected by filtration. The solid was washed with water, $NaHCO_3$ solution and water again. After drying, the desired nitro derivative was obtained as an orange solid (36.8 g).

Step 4: The product obtained in the previous step (129.0 g, 0.42 mol) was dissolved in DMF (400 mL) and DMF-dimethyl acetal (151.6 g, 1.27 mole, 3 equiv.) was added in one portion. The mixture was heated at 110-120° C. under an argon atmosphere until conversion was judged complete by TLC (24 h). The reaction mixture was cooled to room temperature and volatiles removed under vacuum to give a dark colored residue (~180 g). Trituration from ether-THF gave the desired enamine as red crystals (72 g).

Step 5: The enamine obtained in the previous step (72.0 g, 0.20 mol) was dissolved in a mixture of THF (600 mL) and MeOH (600 mL). The dark red solution was heated to 30° C. and Raney-Nickel (18 g) was added to the solution. Hydrazine hydrate (11.6 g, 0.23 mole, 1.15 equiv.) was then added dropwise over 30 min. The reaction temperature was increased to 50° C. and a second portion of hydrazine hydrate (11.6 g, 0.23 mole, 1.15 equiv.) was added over 30 min. After stirring overnight at 50° C., additional Raney-nickel (20 g) and hydrazine hydrate (11.6 g, 0.23 mole, 1.15 equiv.) were added and after stirring for another 7 h at 50° C., the reaction was judged complete by TLC. After cooling, the catalyst was removed by filtration through a pad of celite and the filtrate was evaporated under reduced pressure. The dark brown residue was dissolved in EtOAc (3 L) and the solution washed with water (1.5 L), 10% HCl (1 L) and brine (700 mL). After drying ($Na_2SO_4$), removal of solvents gave the desired bromoindole derivative as a brown solid (35 g).

Step 6: The bromoindole derivative obtained in the previous step (35 g) was dissolved in MeOH (1 L) and triethylamine (16.3 g, 1.2 equiv.) was added followed by 10% Pd/C (1.06 g). The mixture was stirred under hydrogen (35 psi) until completion of the reaction (7 h). The catalyst was then removed by filtration and volatiles removed under reduced pressure. The residue was dissolved in EtOAc (700 mL) and the solution washed with 10% HCl (300 mL), water (350 mL), $NaHCO_3$ (350 mL) and brine. The solution was dried ($Na_2SO_4$) and concentrated under reduced pressure to give the desired indole as a light brown solid (25 g).

This indole derivative was saponified under standard conditions and elaborated to final inhibitors as described in examples 3 and 4.

Example 7

Inhibition of NS5B RNA Dependent RNA Polymerase Activity

The compounds of the invention were tested for inhibitory activity against the hepatitis C virus RNA dependant polymerase (NS5B), according to the protocol described in WO 03/010141.

Example 8

Specificity of NS5B RNA Dependent RNA Polymerase Inhibition

The compounds of the invention were tested for inhibitory activity against polio virus RNA dependent RNA polymerase and calf thymus DNA dependent RNA polymerase II in the format that is described in WO 03/010141 for the HCV polymerase, with the exception that another polymerase was used in place of the HCV NS5B polymerase.

In Tables 1 and 2 below, the following ranges apply:

$IC_{50}$: A=20 µM-1 µM and B<1 µM

The following compounds are prepared, defined by A, B, $R^2$, $R^3$ and Z according to the table 1

TABLE 1
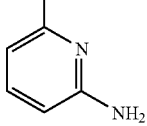
| Cpd. # | A | B | R² | R³ | Z | IC₅₀ | MS (MH⁺) |
|---|---|---|---|---|---|---|---|
| 101 | —N(CH₃)— | =C— | 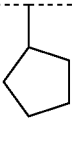 2-aminopyridin-6-yl | 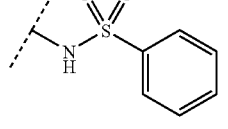 cyclopentyl | 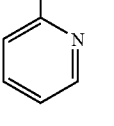 N-H phenylsulfonamide | B | 475.1 |
| 102 | =N— | —N— |  pyridin-2-yl | 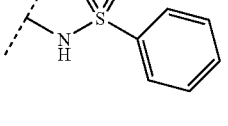 cyclopentyl | 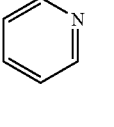 | A | 447.1 |
| 103 | =N— | —N— | 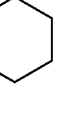 | 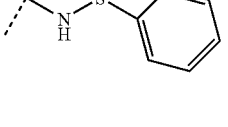 cyclohexyl | 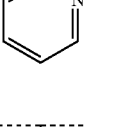 | A | 461.1 |
| 104 | =N— | —N— | 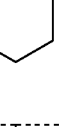 | 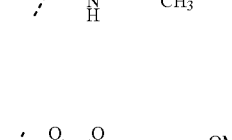 | 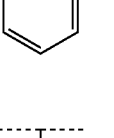 N-methanesulfonamide | A | 399.1 |
| 105 | =N— | —N— | 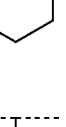 | 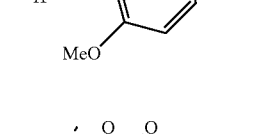 | 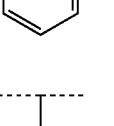 2,5-dimethoxyphenylsulfonamide | A | 521.2 |
| 106 | =N— | —N— |  | 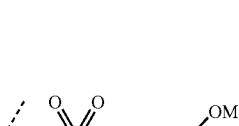 |  | A | 385.1 |
| 107 | =N— | —N— |  | cyclopentyl | 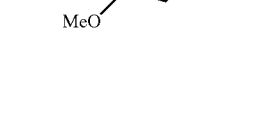 2,5-dimethoxyphenylsulfonamide | B | 507.1 |

TABLE 1-continued
| Cpd. # | A | B | R² | R³ | Z | IC₅₀ | MS (MH⁺) |
|---|---|---|---|---|---|---|---|
| 108 | =N— | —N— |  | 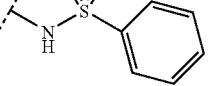 |  | B | 136.1 |
| 109 | =N— | —N— |  | 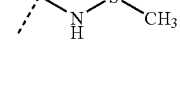 |  | A | 374.1 |
| 110 | =N— | —N— |  | 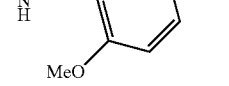 |  | B | 496.1 |
| 111 | =N— | —N— |  | 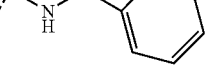 |  | B | 450.1 |
| 112 | =N— | —N— |  | 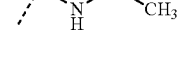 |  | B | 388.1 |
| 113 | =N— | —N— |  | 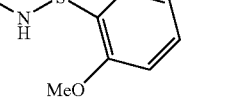 |  | B | 510.1 |
| 114 | —N(CH₃)— | =C— |  | 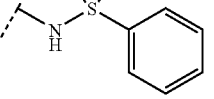 |  | B | 463.1 |
| 115 | —N(CH₃)— | =C— |  | 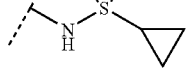 | | B | 413.1 |

TABLE 1-continued
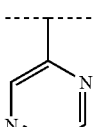
| Cpd. # | A | B | R² | R³ | Z | IC₅₀ | MS (MH⁺) |
|---|---|---|---|---|---|---|---|
| 116 | —N(CH₃)— | =C— | 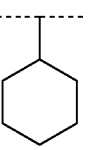 | 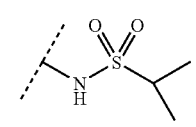 | 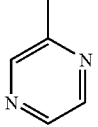 | B | 441.2 |
| 117 | —N(CH₃)— | =C— | 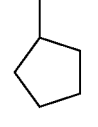 | 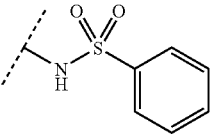 | 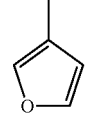 | B | 461.1 |
| 118 | =C(CH₃)— | —N— | 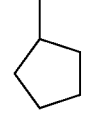 | 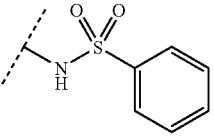 | 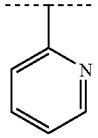 | B | 449.1 |
| 119 | =C(CH₃)— | —N— | 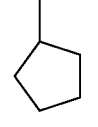 | 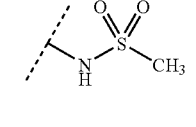 | 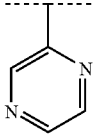 | A | 398.1 |
| 120 | —O— | =C— | 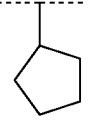 | 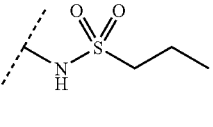 | 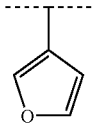 | A | 414.1 |
| 121 | —S— | =C— | 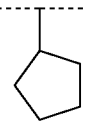 | 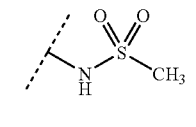 | 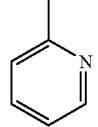 | B | 390.1 |
| 122 | —S— | =C— | 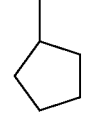 | 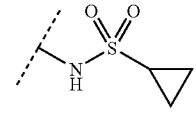 | 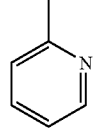 | A | 427.1 |
| 123 | —N(CH₃)— | =C— | 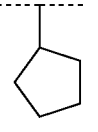 | | 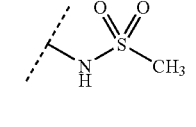 | B | 398.1 |

TABLE 1-continued
| Cpd. # | A | B | R² | R³ | Z | IC$_{50}$ | MS (MH⁺) |
|---|---|---|---|---|---|---|---|
| 124 | —NH— | =C— |  | 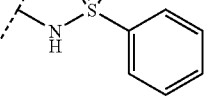 |  | B | 449.2 |
| 125 | —NH— | =C— |  | 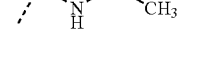 |  | B | 373.1 |
| 126 | —N(CH₃)— | =C— |  | 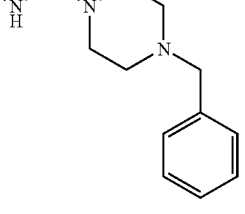 | 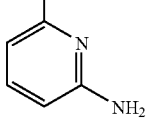 | A | 558.3 |
| 127 | =C(CH₃)— | —N— | 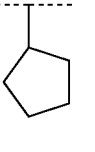 | 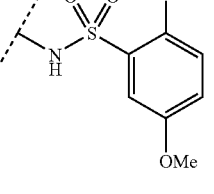 |  | | |
| 128 | —O— | =C— |  | 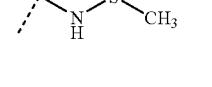 |  | | |
| 129 | —N(CH₃)— | =C— |  | 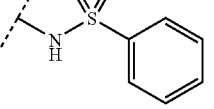 | | | |
The following compounds are prepared, defined by R², R³, R$^{4a}$ and Z according to the table 2. The position number p being 2 or 3 indicates to which C-atom the group C(=O)—Z is bonded.

TABLE 2

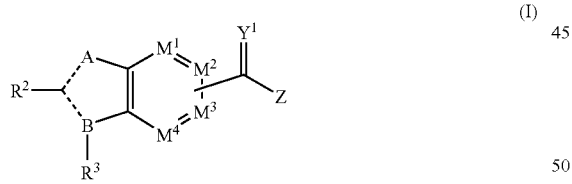

| Cpd. # | R² | R³ | R⁴ᵃ | p | Z | IC₅₀ | MS (MH⁺) |
|---|---|---|---|---|---|---|---|
| 201 | 3-furyl | cyclopentyl | —OCH₃ | 2 | —NH—SO₂—CH₃ | B | 417.1 |
| 202 | 3-furyl | cyclopentyl | —OCH₃ | 2 | —NH—SO₂—Ph | B | 479.1 |
| 203 | 3-furyl | cyclohexyl | —H | 3 | —NH—SO₂—CH₃ | A | 401.1 |
| 204 | 3-furyl | cyclohexyl | —H | 3 | —NH—SO₂—Ph | A | 463.1 |

The invention claimed is:

1. An enantiomer, diastereoisomer, or tautomer of a compound, represented by formula I:

$$(I)$$

wherein
  represents either a single or a double bond;
  B is =C— and A is S;
  the group —C(=Y¹)—Z is covalently linked to either M² or M³,
  M¹ is CR⁴ᵃ,
  M² or M³, when not linked to —C(=Y¹)—Z, is CR⁵,
  M⁴ is CR⁴ᵇ,
  and in addition one or two of the groups selected from M¹, M², M³ and M⁴ may also be N, with the proviso that the group M² or M³ to which —C(=Y¹)—Z is linked is a C-atom,
  Y¹ is O or S;
  Z is defined as NR$^{N2}$—SO₂—R$^C$ or NR$^{N3}$—SO₂—N(R$^{N2}$)R$^{N1}$, wherein R$^C$, R$^{N1}$ or any heterocycle formed by R$^{N1}$ and R$^{N2}$ is optionally substituted with R⁶⁰;
  R² is selected from: halogen or R²¹, wherein R²¹ is aryl or Het, said R²¹ is optionally substituted with R¹⁵⁰;
  R³ is selected from (C₁₋₆)alkyl, (C₃₋₇)cycloalkyl, (C₁₋₃)alkyl-(C₃₋₇)cycloalkyl, (C₅₋₇)cycloalkenyl, (C₁₋₃)alkyl-(C₅₋₇)cycloalkenyl, (C₆₋₁₀)bicycloalkyl, (C₁₋₃)alkyl-(C₆₋₁₀)bicycloalkyl, (C₆₋₁₀)bicycloalkenyl, (C₁₋₃)alkyl-(C₆₋₁₀)bicycloalkenyl, HCy or (C₁₋₃)alkyl-HCy,
    wherein HCy is a saturated or unsaturated 4 to 7-membered heterocyclic group with 1 to 3 heteroatoms selected from O, S and N;
  said alkyl, cycloalkyl, cycloalkenyl, bicycloalkyl, bicycloalkenyl, HCy and alkyl-HCy being optionally substituted with from 1 to 4 substituents selected from:
    a) halogen;
    b) (C₁₋₆)alkyl optionally substituted with:
      1 to 3 substituents selected from halogen;
      OR³¹ or SR³¹ wherein R³¹ is H, (C₁₋₆)alkyl, (C₃₋₇)cycloalkyl or (C₁₋₃)alkyl-(C₃₋₇)cycloalkyl; or
      N(R³²)₂ wherein each R³² is independently H, (C₁₋₆)alkyl, (C₃₋₇)cycloalkyl or (C₁₋₃)alkyl-(C₃₋₇)cycloalkyl; or both R³² are covalently bonded together and to the nitrogen to which they are attached to form a 5, 6 or 7-membered saturated heterocycle;

c) $OR^{33}$ or $SR^{33}$ wherein $R^{33}$ is H, $(C_{1-6})$alkyl, $(C_{3-7})$cycloalkyl or $(C_{1-3})$alkyl-$(C_{3-7})$cycloalkyl;

d) $N(R^{35})_2$ wherein each $R^{35}$ is independently H, $(C_{1-6})$alkyl, $(C_{3-7})$cycloalkyl or $(C_{1-3})$alkyl-$(C_{3-7})$cycloalkyl; or both $R^{35}$ are covalently bonded together and to the nitrogen to which they are attached to form a 5, 6 or 7-membered saturated heterocycle;

$R^{4a}$, $R^{4b}$, $R^5$ each are independently H or defined as $R^{150}$;

$R^{60}$ is defined as 1 to 4 substituents independently selected from:

1 to 3 substituents selected from halogen;

one of each substituent selected from: $OPO_3H$, $NO_2$, cyano, azido, $C(=NH)NH_2$, $C(=NH)NH(C_{1-6})$alkyl or $C(=NH)NHCO(C_{1-6})$alkyl, $SO_3H$; and 1 to 3 substituents selected from:

a) $(C_{1-6})$ alkyl, $(C_{3-7})$cycloalkyl, $(C_{3-7})$ spirocycloalkyl optionally containing 1 or 2 heteroatoms selected from N, O and S; $(C_{2-6})$alkenyl, $(C_{2-8})$alkynyl, $(C_{1-6})$alkyl-$(C_{3-7})$cycloalkyl, all of which optionally being substituted with $R^{150}$;

b) $OR^O$;

c) $OC(O)R^O$;

d) $SR^O$, $SO_2R^C$, $SO_2N(R^{N2})R^{N1}$, $SO_2N(R^{N2})C(O)R^C$, $CONR^{N3}SO_2N(R^{N2})R^{N1}$, or $CONR^{N2}SO_2R^C$;

e) $N(R^{N2})R^{N1}$, $N(R^{N2})COOR^C$, $N(R^{N2})SO_2R^C$ or $N(R^{N1})OR^O$;

f) $N(R^{N2})COR^C$;

g) $N(R^{N3})CON(R^{N2})R^{N1}$;

h) $N(R^{N3})COCOR^C$, $N(R^{N3})COCOOR^O$, $N(R^{N3})CO-CON(R^{N2})OR^O$, or $N(R^{N3})COCON(R^{N2})R^{N1}$;

i) $COR^O$;

j) $COOR^O$;

k) $CON(R^{N2})R^{N1}$;

l) aryl, Het, $(C_{1-4})$alkyl-aryl or $(C_{1-4})$alkyl-Het, all of which optionally being substituted with $R^{150}$;

wherein said $R^{N1}$, $R^C$ and/or $R^O$ are optionally substituted with $R^{150}$ as defined, $R^{150}$ is defined as 1 to 4 substituents independently selected from:

1 to 3 substituents selected from halogen;

one of each substituent selected from: $OPO_3H$, $NO_2$, cyano, azido, $SO_3H$ $C(=NH)NH_2$, $C(=NH)NH(C_{1-6})$alkyl or $C(=NH)NHCO(C_{1-6})$alkyl; and 1 to 3 substituents selected from:

a) $(C_{1-6})$ alkyl, $(C_{3-7})$cycloalkyl, $(C_{3-7})$spirocycloalkyl optionally containing 1 or 2 heteroatoms selected from N, O and S; $(C_{2-6})$alkenyl, $(C_{2-8})$alkynyl, $(C_{1-3})$alkyl-$(C_{3-7})$cycloalkyl, all of which optionally substituted with $R^{160}$;

b) $OR^O$;

c) $OC(O)R^O$;

d) $SR^O$, $SO_2R^C$, $SO_2N(R^{N2})R^{N1}$ or $SO_2N(R^{N2})C(O)R^C$;

e) $N(R^{N2})R^{N1}$, $N(R^{N2})COOR^C$, $N(R^{N2})SO_2R^C$ or $N(R^{N1})OR^O$;

f) $N(R^{N2})COR^C$;

g) $N(R^{N3})CON(R^{N2})R^{N1}$;

h) $N(R^{N3})COCOR^C$, $N(R^{N3})COCOOR^O$, $N(R^{N3})CO-CON(R^{N2})OH$, $N(R^{N3})COCON(R^{N2})O(C_{1-4})$alkyl or $N(R^{N3})COCON(R^{N2})R^{N1}$;

i) $COR^O$;

j) $COOR^O$;

k) tetrazole, triazole, $CONR^{N2}SO_2R^C$, $CONR^{N3}$—$SO_2N(R^{N2})R^{N1}$ or $CON(R^{N2})R^{N1}$;

wherein said $R^{N1}$, $R^C$ and/or $R^O$ are optionally substituted with $R^{160}$ as defined;

$R^{160}$ is defined as 1, 2 or 3 substituents independently selected from:

1, 2 or 3 fluorine substituents; and one of each substituent selected from tetrazole, triazole, chlorine, bromine, iodine, CN, nitro, $(C_{1-4})$alkyl, $OCF_3$, $SCF_3$, $CF_3$, $COOR^{161}$, $SO_3H$, $SR^{161}$, $SO_2R^{163}$, $OR^{161}$, $N(R^{162})_2$, $SO_2N(R^{162})_2$, $SO_2NR^{162}COR^{162}$, $NR^{162}SO_2R^{163}$, —$NR^{161}$—CO—$COOR^{161}$, —$NR^{161}$—CO—CO($NR^{162})_2$, —$CONR^{161}SO_2R^C$, $CONR^{161}$—$SO_2N(R^{162})_2$ or —$SO_2$—$NR^{161}$—$COR^C$, $NR^{162}COR^{162}$ or $CON(R^{162})_2$, wherein $R^{161}$, $R^{163}$ and each $R^{162}$ is independently $(C_{1-4})$alkyl, $(C_{3-7})$cycloalkyl or $(C_{1-3})$alkyl-$(C_{3-7})$cycloalkyl; and $R^{161}$ and each $R^{162}$ may each independently also be H; or both $R^{162}$ are covalently bonded together and to the nitrogen to which they are attached to form a 5, 6 or 7-membered saturated heterocycle;

$R^O$, $R^C$ are independently defined as $(C_{1-6})$alkyl, $(C_{3-7})$cycloalkyl, $(C_{1-4})$alkyl-$(C_{3-7})$cycloalkyl, $(C_{2-6})$alkenyl, aryl, Het, $(C_{1-4})$alkyl-aryl, or $(C_{1-4})$alkyl-Het; or $R^O$ is also optionally defined as H;

$R^{N1}$ is H, $(C_{1-6})$alkyl, $(C_{3-7})$cycloalkyl, $(C_{1-4})$alkyl-$(C_{3-7})$cycloalkyl, $(C_{2-6})$alkenyl, aryl, Het, $(C_{1-4})$alkyl-aryl, $(C_{1-4})$alkyl-Het; and $R^{N2}$, $R^{N3}$, are independently H, $CH_3$, $(C_{2-6})$alkyl, $(C_{3-6})$cycloalkyl, $(C_{1-4})$alkyl-$(C_{3-6})$cycloalkyl; all of which being optionally substituted with halogen, carboxy or $(C_{1-6})$alkoxycarbonyl; and/or wherein said alkyl, cycloalkyl or alkylcycloalkyl is optionally substituted with hydroxy, $(C_{1-6})$alkyl, $(C_{1-6})$alkoxy, amino, —NH$(C_{1-4})$alkyl and/or —N$((C_{1-4})$alkyl$)_2$; or in the case a) of a group $N(R^{N2})R^{N1}$ the substituents $R^{N2}$ and $R^{N1}$; or b) of a group $NR^{N3}$—$N(R^{N2})R^{N1}$ the substituents $R^{N3}$ and $R^{N1}$, or $R^{N2}$ and $R^{N1}$; may be covalently bonded together to form a 4-, 5-, 6- or 7-membered saturated or unsaturated N-containing heterocycle or a 8-, 9-, 10- or 11-membered N-containing heterobicycle, each optionally having additionally from 1 to 3 heteroatoms selected from O, N, and S;

wherein Het is defined as a 4-, 5-, 6- or 7-membered heterocycle having 1 to 4 heteroatoms selected from O, N and S, or a 8-, 9-, 10- or 11-membered heterobicycle having 1 to 5 heteroatoms selected from O, N and S;

or a salt thereof.

2. The compound according to claim 1, wherein represents either a single or a double bond;

B is =C— and A is S;

the group —C($=Y^1$)—Z is covalently linked to either $M^2$ or $M^3$, $M^1$ is $CR^{4a}$, one of $M^2$ and $M^3$ is $CR^5$, $M^4$ is $CR^{4b}$, and in addition one or two of the groups selected from $M^1$, $M^2$, $M^3$ and $M^4$ may also be N, with the proviso that the group $M^2$ or $M^3$ to which —C($=Y^1$)—Z is linked is an C-atom, $Y^1$ is O or S;

Z is defined as $NR^{N2}$—$SO_2$—$R^C$, wherein $R^C$ is optionally substituted with $R^{60}$;

$R^2$ is selected from: halogen or $R^{21}$, wherein $R^{21}$ is aryl or Het, said $R^{21}$ is optionally substituted with $R^{150}$;

$R^3$ is selected from $(C_{1-6})$alkyl, $(C_{3-7})$cycloalkyl, $(C_{1-3})$alkyl-$(C_{3-7})$cycloalkyl, $(C_{5-7})$cycloalkenyl, $(C_{1-3})$alkyl-$(C_{5-7})$cycloalkenyl, $(C_{6-10})$bicycloalkyl, $(C_{1-3})$alkyl-$(C_{6-10})$bicycloalkyl, $(C_{6-10})$bicycloalkenyl, $(C_{1-3})$alkyl-$(C_{6-10})$bicycloalkenyl, HCy or $(C_{1-3})$alkyl-HCy, wherein HCy is a saturated or unsaturated 4 to 7-membered heterocyclic group with 1 to 3 heteroatoms selected from O, S and N;
said alkyl, cycloalkyl, cycloalkenyl, bicycloalkyl, bicycloalkenyl, HCy and alkyl-HCy being optionally substituted with from 1 to 4 substituents selected from:
a) halogen;
b) $(C_{1-6})$alkyl optionally substituted with:
  $OR^{31}$ or $SR^{31}$ wherein $R^{31}$ is H, $(C_{1-6}$alkyl), $(C_{3-7})$cycloalkyl or $(C_{1-3})$alkyl-$(C_{3-7})$cycloalkyl; or
  $N(R^{32})_2$ wherein each $R^{32}$ is independently H, $(C_{1-6})$alkyl, $(C_{3-7})$cycloalkyl or $(C_{1-3})$alkyl-$(C_{3-7})$cycloalkyl; or both $R^{32}$ are covalently bonded together and to the nitrogen to which they are attached to form a 5, 6 or 7-membered saturated heterocycle;
c) $OR^{33}$ or $SR^{33}$ wherein $R^{33}$ is H, $(C_{1-6})$alkyl, $(C_{3-7})$cycloalkyl or $(C_{1-3})$alkyl-$(C_{3-7})$cycloalkyl;
d) $N(R^{35})_2$ wherein each $R^{35}$ is independently H, $(C_{1-6})$alkyl, $(C_{3-7})$cycloalkyl or $(C_{1-3})$alkyl-$(C_{3-7})$cycloalkyl; or both $R^{35}$ are covalently bonded together and to the nitrogen to which they are attached to form a 5, 6 or 7-membered saturated heterocycle;
$R^{4a}$, $R^{4b}$, $R^5$ each are independently H or defined as
$R^{60}$ is defined as 1 to 4 substituents independently selected from:
  1 to 3 substituents selected from halogen;
  one of each substituent selected from: $OPO_3H$, $NO_2$, cyano, azido, $C(=NH)NH_2$, $C(=NH)NH(C_{1-6})$alkyl or $-C(=NH)NHCO(C_{1-6})$alkyl, $SO_3H$; and
  1 to 3 substituents selected from:
  a) $(C_{1-6})$ alkyl, $(C_{3-7})$cycloalkyl, $C_{3-7}$ spirocycloalkyl optionally containing 1 or 2 heteroatom selected from N, O and S; $(C_{2-6})$alkenyl, $(C_{2-8})$alkynyl, $(C_{1-6})$alkyl-$(C_{3-7})$cycloalkyl, all of which optionally being substituted with $R^{150}$;
  b) $OR^O$;
  c) $OC(O)R^O$;
  d) $SR^O$, $SO_2R^C$, $SO_2N(R^{N2})R^{N1}$, $SO_2N(R^{N2})C(O)R^C$ or $CONR^{N2}SO_2R^C$;
  e) $N(R^{N2})R^{N1}$, $N(R^{N2})COOR^C$ or $N(R^{N2})SO_2R^C$;
  f) $N(R^{N2})COR^C$;
  g) $N(R^{N3})CON(R^{N2})R^{N1}$;
  h) $N(R^{N3})COCOR^C$, $N(R^{N3})COCOOR^O$ or $N(R^{N3})COCON(R^{N2})R^{N1}$;
  i) $COR^O$;
  j) $COOR^O$;
  k) $CON(R^{N2})R^{N1}$;
  l) aryl, Het, $(C_{1-4}$alkyl)aryl or $(C_{1-4}$alkyl)Het, all of which optionally being substituted with $R^{150}$;
  wherein said $R^{N1}$, $R^C$ and/or $R^O$ are optionally substituted with $R^{150}$ as defined,
$R^{150}$ is defined as 1 to 4 substituents independently selected from:
  1 to 3 substituents selected from halogen;
  one of each substituent selected from: $OPO_3H$, $NO_2$, cyano, azido, $C(=NH)NH_2$, $C(=NH)NH(C_{1-6})$alkyl or $-C(=NH)NHCO(C_{1-6})$alkyl; and
  1 to 3 substituents selected from:
  a) $(C_{1-6})$ alkyl, $(C_{3-7})$cycloalkyl, $C_{3-7}$ spirocycloalkyl optionally containing 1 or 2 heteroatoms selected from N, O and S; $(C_{2-6})$alkenyl, $(C_{2-8})$alkynyl, $(C_{1-3})$alkyl-$(C_{3-7})$cycloalkyl, all of which optionally substituted with $R^{160}$;
  b) $OR^O$;
  c) $OC(O)R^O$;
  d) $SR^O$, $SO_2R^C$, $SO_2N(R^{N2})R^{N1}$ or $SO_2N(R^{N2})C(O)R^C$;
  e) $N(R^{N2})R^{N1}$, $N(R^{N2})COOR^C$ or $N(R^{N2})SO_2R^C$;
  f) $N(R^{N2})COR^C$;
  g) $N(R^{N3})CON(R^{N2})R^{N1}$;
  h) $N(R^{N3})COCOR^C$, $N(R^{N3})COCOOR^O$ or $N(R^{N3})COCON(R^{N2})R^{N1}$;
  wherein $R^{N1}$ is as defined or OH, OAlkyl;
  i) $COR^O$;
  j) $COOR^O$;
  k) tetrazole or $CON(R^{N2})R^{N1}$;
  wherein said $R^{N1}$, $R^C$ and/or $R^O$ are optionally substituted with $R^{160}$ as defined;
$R^{160}$ is defined as 1, 2 or 3 substituents independently selected from:
  1, 2 or 3 fluorine substituents; and
  one of each substituent selected from tetrazole, chlorine, bromine, iodine, CN, nitro, $C_{1-4}$alkyl, $CF_3$, $COOR^{161}$, $SO_3H$, $SR^{161}$, $SO_2R^{163}$, $OR^{161}$, $N(R^{162})_2$, $SO_2N(R^{162})_2$, $SO_2NR^{162}COR^{162}$, $NR^{162}SO_2R^{163}$, $NR^{162}COR^{162}$ or $CON(R^{162})_2$, wherein $R^{161}$, $R^{163}$ and each $R^{162}$ is independently $(C_{1-4})$alkyl, $(C_{3-7})$cycloalkyl or $(C_{1-3})$alkyl-$(C_{3-7})$cycloalkyl; and $R^{161}$ and each $R^{162}$ may each independently also be H; or both $R^{162}$ are covalently bonded together and to the nitrogen to which they are attached to form a 5, 6 or 7-membered saturated heterocycle;
$R^O$, $R^C$ are independently defined as $(C_{1-6})$alkyl, $(C_{3-6})$cycloalkyl, $(C_{1-4})$alkyl-$(C_{3-6})$cycloalkyl, $(C_{2-6})$alkenyl, aryl, Het, $(C_{1-4})$alkyl-aryl, $(C_{1-4})$alkyl-Het;
$R^{N1}$ is H, $(C_{1-6})$alkyl, $(C_{3-7})$cycloalkyl, $(C_{1-4})$alkyl-$(C_{3-6})$cycloalkyl, $(C_{2-6})$alkenyl, aryl, Het, $(C_{1-4})$alkyl-aryl, $(C_{1-4})$alkyl-Het; or
$R^{N2}$, $R^{N3}$, are independently H, $CH_3$, $(C_{2-6}$alkyl), $(C_{3-6})$cycloalkyl, $(C_{1-4})$alkyl-$(C_{3-6})$cycloalkyl; all of which being optionally substituted with halogen, carboxy or $C_{1-6}$-alkoxycarbonyl; and/or wherein said alkyl, cycloalkyl or alkylcycloalkyl is optionally substituted with hydroxy, $C_{1-6}$-alkyl, $C_{1-6}$-alkoxy, amino, $-NH(C_{1-4}$-alkyl) and/or $-N(C_{1-4}$-alkyl)$_2$; and
in the case
a) of a group $N(R^{N2})R^{N1}$ the substituents $R^{N2}$ and $R^{N1}$; or
b) of a group $NR^{N3}-N(R^{N2})R^{N1}$ the substituents $R^{N3}$ and $R^{N1}$, or $R^{N2}$ and $R^{N1}$; may be covalently bonded together to form a 4-, 5-, 6- or 7-membered saturated or unsaturated N-containing heterocycle or a 8-, 9-, 10- or 11-membered N-containing heterobicycle each may have additionally from 1 to 3 heteroatoms selected from O, N, and S, wherein said heterocycle or heterobicycle is optionally substituted as defined;
wherein Het is defined as a 4-, 5-, 6- or 7-membered heterocycle having 1 to 4 heteroatoms selected from O, N and S, or a 8-, 9-, 10- or 11-membered heterobicycle having 1 to 5 heteroatoms selected from O, N and S;
or a salt thereof.

3. The compound according to claim 1 which is

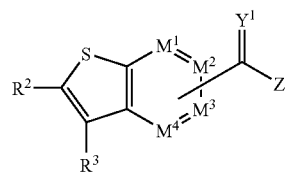

wherein $R^1$, $R^2$, $R^3$, $Y^1$, Z, $M^1$, $M^2$, $M^3$ and $M^4$ are defined as in claim 1.

4. The compound according to claim 1, wherein $R^1$ is selected from the group consisting of: H and $(C_{1-6})$alkyl.

5. The compound according to claim 4, wherein $R^1$ is H, $CH_3$, ethyl, or isobutyl.

6. The compound according to claim 5, wherein $R^1$ is H or $CH_3$.

7. The compound according to claim 6, wherein $R^1$ is $CH_3$.

8. The compound according to claim 1, wherein $Y^1$ is O.

9. The compound according to claim 1, wherein Z is $NR^{N3}$—$SO_2$—$N(R^{N2})R^{N1}$, wherein $R^{N1}$ or any heterocycle formed by $R^{N1}$ and $R^{N2}$ is optionally substituted with $R^{60}$, and wherein $R^{N3}$, $R^{N2}$, $R^{N1}$ and $R^{60}$ are defined as in claim 1.

10. The compound according to claim 1, wherein Z is $NR^{N2}$—$SO_2$—$R^C$, wherein $R^C$ is optionally substituted with $R^{60}$, and wherein Het, $R^{N2}$, $R^C$ and $R^{60}$ are defined as in claim 1.

11. The compound according to claim 10, wherein Z is NH—$SO_2$—$R^C$, wherein $R^C$ is selected from the group consisting of $(C_{1-6})$alkyl, $(C_{3-6})$cycloalkyl, $(C_{1-3})$alkyl-$(C_{3-6})$cycloalkyl, $(C_{2-6})$ alkenyl, phenyl, naphthyl, Het, $(C_{1-3})$alkyl-phenyl, $(C_{1-3})$alkyl-naphthyl, $(C_{1-3})$alkyl-Het, wherein said alkyl, cycloalkyl, alkyl-cycloalkyl, alkenyl, phenyl, naphthyl, Het, alkyl-phenyl, alkyl-naphthyl, or alkyl-Het, are all optionally substituted with 1 to 4 substituents selected from $R^{60}$, wherein $R^{60}$ and Het are defined as in claim 10.

12. The compound according to claim 11, wherein Z is NH—$SO_2$—$R^C$, wherein $R^C$ is selected from the group consisting of methyl, ethyl, n-propyl, i-propyl, cyclopropyl, cyclobutyl, cyclopentyl, cyclopropylmethyl, cyclobutylmethyl, cyclopentylmethyl, pyrrolidine, piperidine, morpholine, thiomorpholine, piperazine, phenyl, naphthyl, benzyl, thiophene, furan, pyrrole, imidazole, pyrazole, oxazole, isoxazole, thiazole, pyridazine, pyrimidine, pyrazine, diazepine, azepine, quinoline, isoquinoline, benzofuran, benzothiophene, benzothiazole, purine, pteridine, 2,1,3-benzothiadiazole

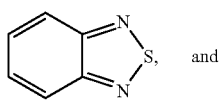

and imidazo[2,1-B][1,3]thiazole

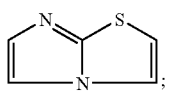

;

all of which are optionally substituted with 1 to 3 substituents selected from $R^{60}$, wherein $R^{60}$ is defined as in claim 11.

13. The compound according to claim 1, wherein $R^2$ is $R^{21}$ wherein $R^{21}$ is phenyl or Het selected from the group of formulas

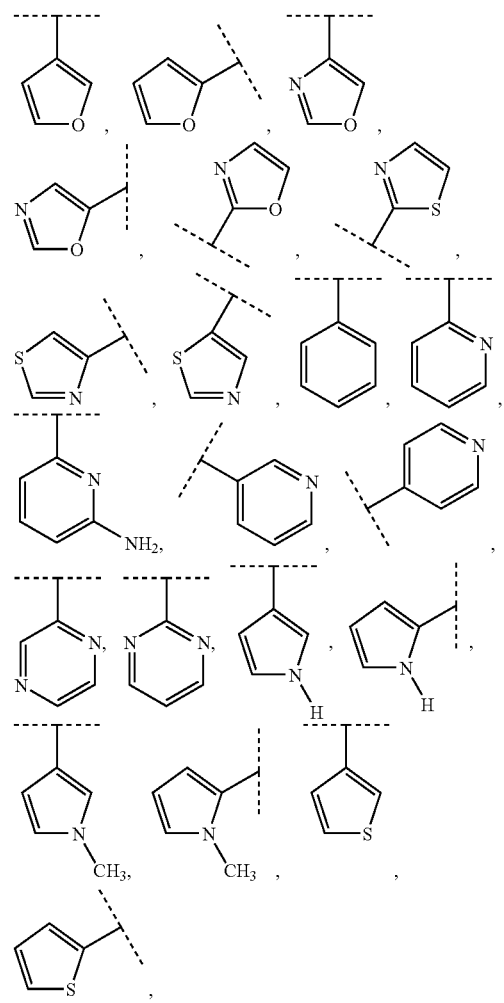

and wherein said $R^{21}$ is unsubstituted or substituted with $R^{150}$, being defined as in claim 1.

14. The compound according to claim 1, wherein $R^2$ is $R^{21}$ wherein $R^{21}$ is defined as in claim 1, and wherein $R^{21}$ is optionally substituted with 1, 2 or 3 substituents selected from:

1 to 3 substituents selected from halogen;

one of each substituent selected from: $NO_2$, cyano, azido; and 1 to 2 substituents selected from:

a) $(C_{1-4}$alkyl or $(C_{1-4}$alkoxy, both optionally substituted with OH, $O(C_{1-4})$alkyl, $SO_2(C_{1-4})$alkyl), 1 to 3 halogen atoms, amino, $NH(C_{1-4})$alkyl) or $N((C_{1-4})$alkyl$)_2$;

b) $NR^{111}R^{112}$ wherein both $R^{111}$ and $R^{112}$ are independently H, $(C_{1-4})$alkyl, or $R^{112}$ is $(C_{3-7})$cycloalkyl, $(C_{1-3})$ alkyl$(C_{3-7})$cycloalkyl, phenyl, benzyl; or both $R^{111}$ and $R^{112}$ are covalently bonded together and to the nitrogen to which they are attached to form a nitrogen-containing heterocycle, each of said alkyl, cycloalkyl, alkylcycloalkyl, phenyl and benzyl, being optionally substituted with halogen or:

—$OR^{2h}$ or $N(R^{2h})_2$, wherein each $R^{2h}$ is independently H, $(C_{1-4})$alkyl, or both $R^{2h}$ are covalently bonded together and to the nitrogen to which they are attached to form a nitrogen-containing heterocycle;

c) NHCOR$^{117}$ wherein R$^{117}$ is (C$_{1-4}$)alkyl, O(C$_{1-4}$)alkyl or O(C$_{3-7}$)cycloalkyl; and
e) CONH$_2$, CONH(C$_{1-4}$alkyl), CON((C$_{1-4}$alkyl)$_2$.

15. The compound according to claim 1, wherein R$^3$ is selected from (C$_{3-7}$)cycloalkyl, (C$_{5-7}$)cycloalkenyl, (C$_{6-10}$)bicycloalkyl, (C$_{6-10}$)bicycloalkenyl, or Het, wherein said groups are unsubstituted or mono- or disubstituted by halogen, cyano, nitro, hydroxy, (C$_{1-4}$)alkyl and/or O—(C$_{1-4}$) alkyl, wherein the alkyl groups may be fluorinated.

16. The compound according to claim 15, wherein R$^3$ is cyclopropyl, cyclobutyl, cyclopentyl, cyclohexyl or cycloheptyl, or a group selected from

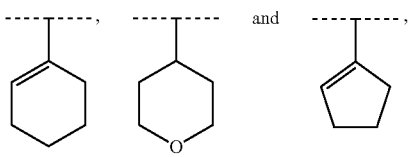

wherein all said groups are unsubstituted or substituted by fluorine, (C$_{1-3}$)alkyl or CF$_3$.

17. The compound according to claim 16, wherein R$^3$ is cyclopentyl or cyclohexyl.

18. The compound according to claim 1 wherein R$^{4a}$, R$^{4b}$, R$^5$ each are independently H, hydroxy, halogen, cyano, nitro, carboxyl, (C$_{1-4}$)alkyl, CF$_3$, (C$_{1-4}$)alkoxy, —O—(C$_{3-7}$)cycloalkyl, —O—(C$_{1-3}$)alkyl-(C$_{3-7}$)cycloalkyl, —O-aryl, —O—(C$_{1-3}$)alkyl-aryl, —O-Het, —O—(C$_{1-3}$)alkyl-Het, NR$^{N1}$R$^{N2}$, COR$^O$, NR$^{N2}$COR$^C$, CONR$^{N2}$R$^{N1}$, or NR$^{N3}$CONR$^{N1}$R$^2$;
  wherein Het, R$^C$, R$^O$, R$^{N1}$, R$^{N2}$, R$^{N3}$ and R$^{160}$ are as defined in claim 1; and
  wherein all said alkyl groups, including alkoxy, may be mono-, di- or trisubstituted by fluorine or mono-substituted by chlorine or bromine.

19. The compound according to claim 18 wherein R$^C$, R$^O$ and R$^{N1}$ are independently of each other H, (C$_{1-4}$)alkyl, aryl, (C$_{1-3}$)alkyl-aryl;
  wherein aryl is defined as phenyl optionally substituted with R$^{160}$, wherein R$^{160}$ is defined as in claim 18; and
  wherein all said alkyl groups may be mono-, di- or trisubstituted by fluorine or mono-substituted by chlorine or bromine; and
  wherein R$^{N2}$ and R$^{N3}$ are independently H or methyl.

20. The compound according to claim 18 wherein R$^{4a}$, R$^{4b}$, R$^5$ each are independently H, hydroxy, halogen, cyano, nitro, methyl, CF$_3$, methoxy, carboxy, amino, —NMe$_2$, —CONH$_2$, —NHCONH$_2$, —CO—NHMe, —NHCONHMe, —CO-NMe$_2$ or —NHCONMe$_2$.

21. The compound according to claim 20 wherein R$^{4a}$, R$^{4b}$, R$^5$ each are H, methyl or methoxy.

22. The compound according to claim 1 wherein R$^{4a}$ is H or methyl.

23. The compound according to claim 1 wherein at least two of the substituents selected from R$^{4a}$, R$^{4b}$, R$^5$ are H.

24. The compound according to claim 1, wherein R$^{60}$ is each defined as 1 to 4 substituents independently selected from:
  1 to 3 substituents selected from halogen;
  one of each substituent selected from: NO$_2$, cyano, azido; and
  1 to 3 substituents selected from:
  a) (C$_{1-4}$) alkyl, (C$_{3-7}$)cycloalkyl, (C$_{2-4}$)alkenyl, (C$_{2-4}$)alkynyl, (C$_{1-3}$)alkyl-(C$_{3-7}$)cycloalkyl, all of which optionally being substituted with R$^{150}$;
  b) OR$^O$;
  e) N(R$^{N2}$)R$^{N1}$;
  f) N(R$^{N2}$)COR$^C$;
  j) COOR$^O$;
  k) CON(R$^{N2}$)R$^{N1}$;
  l) phenyl, Het, (C$_{1-3}$alkyl)phenyl or (C$_{1-3}$alkyl)Het; wherein
    Het is selected from furan, tetrahydrofuran, thiophene, tetrahydrothiophene, tetrahydropyran, pyridinyl, azetidine, pyrrolidine, piperidine, piperazine, morpholine, thiomorpholine, homopiperidine and homopiperazine, all of which optionally being substituted with R$^{150}$;
  wherein said R$^{N1}$, R$^C$ and/or R$^O$ are optionally substituted with R$^{150}$ as defined,
  and R$^{150}$, R$^{N1}$, R$^{N2}$, R$^C$ and R$^O$ are defined as in claim 1.

25. The compound according to claim 1, wherein R$^{150}$ is defined as 1 to 4 substituents independently selected from:
  1 to 3 fluorine-substituents;
  one of each substituent selected from: chlorine, bromine, iodine, NO$_2$, cyano, azido; and
  1 to 3 substituents selected from:
  a) (C$_{1-3}$) alkyl, CF$_3$, (C$_{3-6}$)cycloalkyl, (C$_{1-3}$) alkyl-(C$_{3-6}$)cycloalkyl, all of which optionally substituted with R$^{160}$;
  b) OR$^O$;
  e) N(R$^{N2}$)R$^{N1}$;
  f) N(R$^{N2}$)COR$^C$;
  j) COOR$^O$;
  k) CON(R$^{N2}$)R$^{N1}$;
  wherein said R$^{N1}$, R$^C$ and/or R$^O$ are optionally substituted with R$^{160}$ as defined; and
  R$^{160}$, R$^{N1}$, R$^{N2}$, R$^C$ and R$^O$ are defined as in claim 1.

26. The compound according to claim 1, wherein R$^{160}$ is defined as 1, 2 or 3 substituents independently selected from:
  1, 2 or 3 fluorine substituents; and
  one of each substituent selected from chlorine, bromine, iodine, CN, nitro, methyl, trifluoromethyl, ethyl, n-propyl, i-propyl, COOH, COOCH$_3$, OH, OCH$_3$, OCF$_3$, NH$_2$, NHCH$_3$, N(CH$_3$)$_2$, SO$_2$NH$_2$, SO$_2$NHCOCH$_3$, NHCOCH$_3$ or CONH$_2$, CONHCH$_3$ and CON(CH$_3$)$_2$.

27. The compound according to claim 1, wherein
R$^O$, R$^C$ are independently defined as (C$_{1-4}$)alkyl, (C$_{3-6}$)cycloalkyl, (C$_{1-3}$)alkyl-(C$_{3-6}$)cycloalkyl, phenyl, benzyl, Het, (C$_{1-3}$)alkyl-Het; all of which are optionally substituted as defined; and R$^O$ may also be H;
R$^{N1}$ is H, (C$_{1-4}$)alkyl, (C$_{3-6}$)cycloalkyl, (C$_{1-3}$)alkyl-(C$_{3-6}$)cycloalkyl, phenyl, benzyl, phenylethyl, Het, (C$_{1-3}$) alkyl-Het; wherein said alkyl, cycloalkyl, alkyl-cycloalkyl, phenyl, benzyl, phenylethyl, Het and alkyl-Het are optionally substituted as defined; or
R$^{N2}$, R$^{N3}$, are independently H, methyl, ethyl, n-propyl, i-propyl, cyclopropyl, cyclopropylmethyl; all of which being optionally substituted with fluorine, carboxy or methoxycarbonyl; and/or wherein said ethyl, n-propyl or i-propyl is optionally substituted with hydroxy, methyl, methoxy, amino, —NH(CH$_3$) and/or —N(CH$_3$)$_2$; and in the case a) of a group $N(R^{N2})R^{N1}$ the substituents $R^{N2}$ and $R^{N1}$ or b) of a group $NR^{N3}$—$N(R^{N2})R^{N1}$ the substituents $R^{N3}$ and $R^{N1}$ or $R^{N2}$ and $R^{N1}$ may be covalently bonded together to form a 5-, 6- or 7-membered saturated heterocycle which may have additionally one heteroatom selected from O, N, and S, wherein said heterocycle is optionally substituted as defined;

wherein Het is defined as in claim 1.

28. A method of treating HCV infection in a mammal, comprising administering to the mammal an effective amount of a compound of formula I according to claim 1 or a pharmaceutically acceptable salt thereof, as an inhibitor of HCV polymerase.

29. A method of treating HCV infection in a mammal, comprising administering to the mammal an effective amount of a compound of formula I according to claim 1 or a pharmaceutically acceptable salt thereof, as an inhibitor of RNA dependent RNA polymerase activity of the enzyme NS5B, encoded by HCV.

30. A method of treating HCV infection in a mammal, comprising administering to the mammal an effective amount of a compound of formula I according to claim 1 or a pharmaceutically acceptable salt thereof, as an inhibitor of HCV replication.

31. A pharmaceutical composition for the treatment of HCV infection, comprising an effective amount of a compound of formula I according to claim 1 or a pharmaceutically acceptable salt thereof, and a pharmaceutically acceptable carrier.

32. The composition according to claim 31 further comprising a therapeutically effective amount of one or more antiviral agents.

33. The composition according to claim 32, wherein said antiviral agent is selected from: ribavirin and amantadine.

34. The composition according to claim 32 wherein the antiviral agent is an other anti-HCV agent.

35. The pharmaceutical composition according to claim 34, wherein the other anti-HCV agent is an immunomodulatory agent, in particular selected from $\beta$-, $\delta$-$\gamma$-, and $\omega$-interferon.

36. A composition according to claim 34, wherein said anti-HCV agent is another inhibitor of HCV polymerase.

37. The composition according to claim 34, wherein the other anti-HCV agent is an inhibitor of HCV NS3 protease.

38. The composition according to claim 34, wherein the other anti-HCV agent is an inhibitor of another target in the HCV life cycle.

39. A composition according to claim 38, wherein said inhibitor of another target in the HCV life cycle is an agent that inhibits a target selected from HCV helicase, HCV NS2/3 protease and HCV IRES.

\* \* \* \* \*